US010752966B2

(12) United States Patent
Storch et al.

(10) Patent No.: US 10,752,966 B2
(45) Date of Patent: Aug. 25, 2020

(54) METHODS AND COMPOSITIONS FOR DETECTION OF ENTEROVIRUS D68

(71) Applicant: Washington University, St. Louis, MO (US)

(72) Inventors: Gregory A. Storch, St. Louis, MO (US); Todd N. Wylie, St. Louis, MO (US); Kristine M. Wylie, St. Louis, MO (US)

(73) Assignee: Washington University, St. Louis, MO (US)

( * ) Notice: Subject to any disclaimer, the term of this patent is extended or adjusted under 35 U.S.C. 154(b) by 318 days.

(21) Appl. No.: 15/137,430

(22) Filed: Apr. 25, 2016

(65) Prior Publication Data

US 2016/0312314 A1 Oct. 27, 2016

Related U.S. Application Data

(60) Provisional application No. 62/152,671, filed on Apr. 24, 2015.

(51) Int. Cl.
*C12Q 1/68* (2018.01)
*C12Q 1/70* (2006.01)
*C12Q 1/6806* (2018.01)

(52) U.S. Cl.
CPC .......... *C12Q 1/701* (2013.01); *C12Q 1/6806* (2013.01)

(58) Field of Classification Search
None
See application file for complete search history.

(56) References Cited

PUBLICATIONS

From CDC website: Assay instructions dated Oct. 14, 2014 for Enterovirus D68 (EV0D68) 2014 Outbreak Strain-Specific Real-Time Reverse Transcription/Polymerase Chain Reaction (rRT-PCR) pp. 1-13.*
Molecular Diagnostics (Real Time PCR Design, from Molecular Diagnostics: Current Research and Applications; Caister Academic Press; ed., Jim Huggett and Justin O'Grady; May 2014).*
Genbank Accession No. KM851225.1 (NCBI, NLM 2014).*
Bustin et al; Biomolecular Detection and Quantification, vol. 14, 2017, pp. 19-28.*
Altschul, S. et al., "Basic Local Alignment Search Tool," J. Mol. Biol., 1990, pp. 403-410, vol. 215, Academic Press Limited.
Boratyn, G. et al., "BLAST: a more efficient report with usability improvements," Nucleic Acids Res., 2013, pp. W29-W33, vol. 41, Oxford University Press.
Centers for Disease Control and Prevention, "Clusters of Acute Respiratory Illness Associated with Human Enterovirus 68—Asia, Europe, and United States, 2008-2010," Morbidity and Mortality Weekly Report, Sep. 30, 2011, pp. 1301-1304, vol. 60, No. 38.
Colvin, J. et al., "Detection of Viruses in Young Children with Fever Without an Apparent Source," Pediatrics, 2012, pp. e1455-e1462, vol. 130, No. 6.
Edgar, R. et al., "MUSCLE: multiple sequence alignment with high accuracy and high throughput," Nucleic Acids Res., 2004, pp. 1792-1797, vol. 32, No. 5, Oxford University Press.
"Enterovirus D68," United States Outbreak 2014, Centers for Disease Control and Prevention web page https://www.cdc.gov/non-polio-enterovirus/about/ev-d68.html, page last updated Jul. 19, 2016, 6 pgs.
Federal Register, Feb. 27, 2015, pp. 10685-10686, vol. 80, No. 39.
GenBank Accession No. KM881710.2, BioProject: PRJNA263037, Jan. 16, 2015, 4 pgs.
Huson, D. et al., "Design of a compartmentalized shotgun assembler for the human genome," Bioinformatics, 2001, pp. S132-S139, vol. 17, Suppl. 1, Oxford University Press.
Imamura, T. et al., "Global reemergence of enterovirus D68 as an important pathogen for acute respiratory infections," Rev. Med. Virol., 2015, pp. 102-114, vol. 25, John Wiley & Sons Ltd.
Johnson, M. et al., "NCBI BLAST: a better web interface," Nucleic Acids Res., 2008, pp. W5-W9, vol. 36.
Kurtz, S. et al., "A new method to compute K-mer frequencies and its application to annotate large repetitive plant genomes," BMC Genomics, 2008, pp. 1-18, vol. 9, No. 517, BioMed Central Ltd.
Lee, W-M. et al., "A Diverse Group of Previously Unrecognized Human Rhinoviruses Are Common Causes of Respiratory Illnesses in Infants," PloS One, Oct. 2007, pp. 1-11, vol. 2, No. 10, e966.
Midgley, C. et al., "Severe Respiratory Illness Associated with Enterovirus D68—Missouri and Illinois, 2014," Centers for Disease Control and Prevention, Morbidity and Mortality Weekly Report, Sep. 12, 2014, pp. 798-799, vol. 63, No. 36.
Nijhuis, M. et al., "Rapid and Sensitive Routine Detection of All Members of the Genus Enterovirus in Different Clinical Specimens by Real-Time PCR," J. Clin. Microbiol., Oct. 2002, pp. 3666-3670, vol. 40, No. 10, American Society for Microbiology.
Nix, W. et al., "Sensitive, Seminested PCR Amplification of VP1 Sequences for Direct Identification of All Enterovirus Serotypes from Original Clinical Specimens," J. Clin. Microbiol., Aug. 2006, pp. 2698-2704, vol. 44, No. 8.
Oberste, M. et al., "Enterovirus 68 is associated with respiratory illness and shares biological features with both the enteroviruses and the rhinoviruses," J. Gen. Virol., 2004, pp. 2577-2584, vol. 85, No. 9, SGM, Great Britain.
Oberste, M. et al., "Typing of Human Enteroviruses by Partial Sequencing of VP1," J. Clin. Microbiol., May 1999, pp. 1288-1293, vol. 37, No. 5.
Piralla, A. et al., "A New Real-Time Reverse Transcription-PCR Assay for Detection of Human Enterovirus 68 in Respiratory Samples," J. Clin. Microbiol., May 2015, pp. 1725-1726, vol. 53, No. 5.
Quinlan, A. et al., "BEDTools: a flexible suite of utilities for comparing genomic features," Bioinformatics, 2010, pp. 841-842, vol. 26, No. 6, Oxford University Press.
Rahamat-Langendoen, J. et al., "Upsurge of human enterovirus 68 infections in patients with severe respiratory tract infections," J. Clin. Virol., 2011, pp. 103-106, vol. 52, Elsevier B.V.
Schieble, J. et al., "A Probable New Human Picornavirus Associated With Respiratory Disease," Am. J. Epidemiol., 1967, pp. 297-310, vol. 85, No. 2, The Johns Hopkins University, U.S.A.

(Continued)

*Primary Examiner* — Jehanne S Sitton
(74) *Attorney, Agent, or Firm* — Polsinelli PC

(57) ABSTRACT

The present disclosure is directed to improved methods and compositions for the detection of enterovirus D68.

13 Claims, 3 Drawing Sheets
(3 of 3 Drawing Sheet(s) Filed in Color)

Specification includes a Sequence Listing.

(56) References Cited

PUBLICATIONS

Sutton, G. et al., "TIGR Assembler: A New Tool for Assembling Large Shotgun Sequencing Projects," Genome Sci. Technol., 1995, pp. 9-19, vol. 1, No. 1, Mary Ann Liebert, Inc.
Tokarz, R. et al., "Worldwide emergence of multiple clades of enterovirus 68," J. Gen. Virol., 2012, pp. 1952-1958, vol. 93, SGM, Great Britain.
Wylie, K. et al., "Genome sequence of enterovirus D68 from St. Louis, Missouri, USA," Emerging Infect. Dis., Jan. 2015, pp. 184-186, vol. 21, No. 1.
Xiao, M. et al., "DNA Analysis by Fluorescence Quenching Detection," Genome Res., 2003, pp. 932-939, vol. 13, Cold Spring Harbor Laboratory Press.

* cited by examiner

METHODS AND COMPOSITIONS FOR DETECTION OF ENTEROVIRUS D68

CROSS REFERENCE TO RELATED APPLICATIONS

This application claims the benefit of U.S. Provisional Application No. 62/152,671, filed Apr. 24, 2015 the disclosure of which is hereby incorporated by reference in its entirety.

GOVERNMENTAL RIGHTS

This invention was made with government support under AI097213 awarded by the National Institutes of Health. The government has certain rights in the invention.

FIELD OF THE INVENTION

The present disclosure is directed to improved methods and compositions for the detection of enterovirus D68.

BACKGROUND OF THE INVENTION

Human enterovirus D68 (EV-D68) was first isolated from samples obtained in California in 1962 from four children with pneumonia and bronchiolitis. The type strain isolated from one of these children has been designated the Fermon strain. Subsequently, only small numbers of EV-D68 cases were reported until the early 2000s. However, from 2008-12 outbreaks in Japan, the Philippines, the Netherlands, and the USA (Georgia, Pennsylvania, and Arizona) have revealed EV-D68 as an emerging pathogen capable of causing severe respiratory illness. During the 2014 enterovirus/rhinovirus season in the United States, EV-D68 circulated at an unprecedented level. From August 2014 to January 2015, CDC and state public health laboratories confirmed a total of 1,153 cases of respiratory illness caused by EV-D68, with at least 14 deaths. Infected individuals were primarily children, and resided in 49 states and the District of Columbia. The CDC has also reported there were likely millions of EV-D68 infections in which the etiology was not determined.

In mid-August of 2014, hospitals in Missouri and Illinois noticed an increased number of patients with severe respiratory illness and reported the presence of EV-D68. Because efforts to define the outbreak were hampered by the lack of a test for EV-D68 that did not require nucleotide sequencing, there is a need in the art for a rapid, specific RT-PCR assay.

SUMMARY OF THE INVENTION

In an aspect, the disclosure provided methods for detection of enterovirus D68 in a sample. The method comprises: (a) contacting a nucleic acid obtained from the sample with an oligonucleotide primer comprising the sequence 5'-CACYGAACCAGARGAAGCCA-3' (SEQ ID NO:3) and an oligonucleotide primer comprising the sequence 3'-AARGAATCATCCCGTCGAAATC-5' (SEQ ID NO:4); (b) exposing the contacted sample to a DNA amplification process that provides for production of a 98 nucleotide amplification product of the enterovirus D68 VP1 gene; and (c) detecting the 98 nucleotide amplification product, wherein the presence of said amplification product indicates that the sample contained enterovirus D68.

In another aspect, the disclosure provides methods for detection of enterovirus D68 in a sample. The method comprises: (a) contacting a nucleic acid obtained from the sample with an oligonucleotide primer pair capable of annealing to a sequence contained with to residues 2475 to 2572 of the enterovirus D68 sequence of SEQ ID NO:1 and providing a DNA amplification product therefrom of at least about 50 nucleotides to 98 nucleotides in length; (b) exposing the contacted sample to a DNA amplification process that provides for production of a nucleotide amplification product of the enterovirus D68 VP1 gene; and (c) detecting the amplification product, wherein the presence of said amplification product indicates that the sample contained enterovirus D68.

BRIEF DESCRIPTION OF THE FIGURES

The application file contains at least one drawing executed in color. Copies of this patent application publication with color drawing(s) will be provided by the Office upon request and payment of the necessary fee.

FIG. 1A: L1 primer (SEQ ID NO:3-CACYGAACCAGAR-GAAGCCA); P1 probe (SEQ ID NO:12-TCGCACAGT-GATAAATCAGCAYGG); R1 & R2 primers (SEQ ID NO:10-5'-CCAAAGCTGCTCTACTGAGAAA-3' and SEQ ID NO:11-5'-CTAAAGCTGCCCTACTAAGRAA-3'); Enterovirus nucleotide 2465 sense strand (SEQ ID NO:13-5'- . . . CAACTTCTAACACTGAACCAGAAGAAGC-CATACAAACTCGCACAGTGATAAATCA GCACGGT-GTATCCGAGACTCTAGTGGAGAATTTTCTCAGTAG AGCAGCTTTGGT . . . -3'); Enterovirus nucleotide 2465 antisense strand (SEQ ID NO:14-5'- . . . ACCAAAGCT-GCTCTACTGAGAAAATTCTCCACTAGAGTCTCGGA-TACACCGTGCT GATTTATCACTGTGCGAGTTTG-TATGGCTTCTTCTGGTTCAGTGTTAGAAGTTG . . . -3'). FIG. 1B, FIG. 1C: L1 primer (SEQ ID NO:15-CAAACTCGCACAGTGATAAAYCARCA); P1 probe (SEQ ID NO:16-CTGTTCTTGAAAAAGTTTACCTG); R1 primer (SEQ ID NO:17-5'-GTATTATTACTACTAC-CATTCACNGCNAC-3'); Enterovirus nucleotide 2465 sense strand (SEQ ID NO:18-5'- . . . AACTTCTAACACT-GAACCAGAAGAAGCCATACAAACTCGCACAGTGA-TAAATCAG CACGGTGTATCCGAGACTCTAGTGGA-GAATTTTCTCAGTAGAGCAGCTTTGGTATC AAAGAGAAGTTTTGAATACAAAGATCATACT-TCGTCTGCAGCACAAGCAGACAAGA ACTTTTTCAAATGGACAATTAACACCAGATCCTTT-GTACAGTTAAGAAGAAAATTAG AATTATTCACAT-ACCTTAGATTTGATGCTGAGATCACTATACTCA-CAACTGTAGCAG TGAATGGTAGTGGTAATAATACATACGTGGGT . . . -3'); Enterovirus nucleotide 2465 antisense strand (SEQ ID NO:19-5'- . . . ACCCACGTATGTATTATTACCACTAC-CATTCACTGCTACAGTTGTGAGTATAGTG ATCTCA-GCATCAAATCTAAGGTATGTGAATAAT-TCTAATTTTCTTCTTAACTGTACAA AGGATCTGGTGTTAATTGTCCATTTGAAAAAGT-TCTTGTCTGCTTGTGCTGCAGACG AAGTAT-GATCTTTGTATTCAAAACTTCTCTTTGATAC-CAAAGCTGCTCTACTGAGAA AATTCTCCACTAGAGTCTCGGATACACCGTGCT-GATTTATCACTGTGCGAGTTTGTA TGGCTTCTTCTG-GTTCAGTGTTAGAAGTTG . . . -3'). Y=T, C; R=G, A; N=A, T, C, G.

DETAILED DESCRIPTION OF THE INVENTION

Figure 1A:
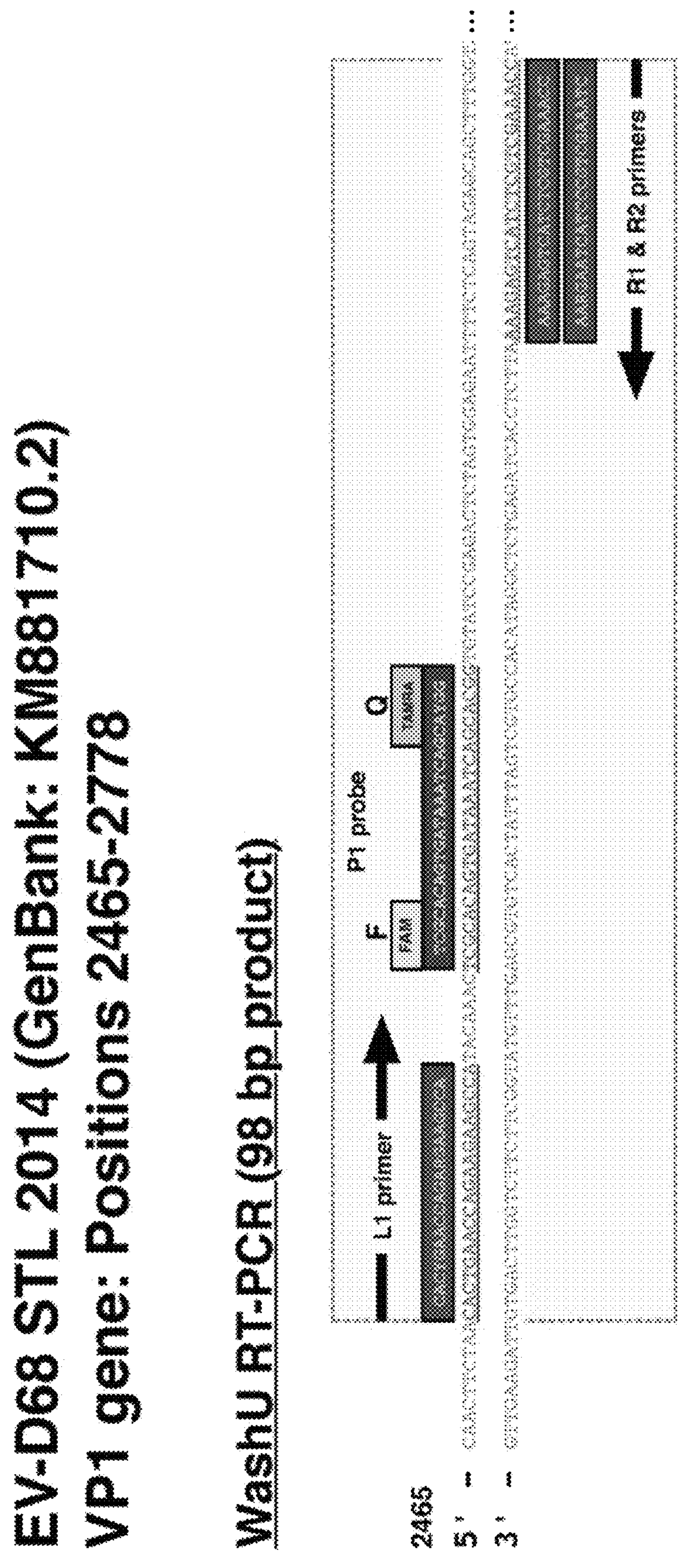
FIG. 1A, FIG. 1B and FIG. 1C depict WashU and CDC RT-PCR design comparison. Shown here are WashU (FIG. 1A) and CDC (FIG. 1B, FIG. 1C) RT-PCR primer and probe sequences and their locations along the EV-D68 St. Louis 2014 (GenBank: KM881710.2) reference genome.

Disclosed herein is a real-time reverse transcription PCR (RT-PCR) assay for detection of human enterovirus D68 (EV-D68) in clinical specimens. This assay was developed in response to the unprecedented 2014 nationwide EV-D68 outbreak associated with severe respiratory illness in the United States. During evaluation of the outbreak, the genome sequence of the EV-D68 virus circulating in St. Louis, Mo. was sequenced (Wylie et al. *Emerging Infect Dis* 2015; 21(1): 184-186, the disclosure of which is hereby incorporated by reference in its entirety). This sequence, along with other GenBank® sequences from past EV-D68 occurrences, was used to computationally select a region of EV-D68 appropriate for targeting in a strain-specific RT-PCR assay. The RT-PCR assay that was developed and disclosed herein amplifies a segment of the VP-1 gene. This assay exhibits improved sensitivity compared to the EV-D68-specific RT-PCR assay released in October of 2014 by the CDC, as well as to a number of commercially available assays that broadly detect enteroviruses/rhinoviruses, including three multiplex respiratory panels approved for clinical use by the FDA. It was also more sensitive for detection of the 2014 US outbreak virus than a recently described assay that amplifies a segment of the 5'-nontranslated region of the viral genome. The assay provides complete EV-D68 specificity and detects divergent strains, including the first EV-D68 strain (Fermon) identified in California in 1962. This assay should be useful for identifying and studying current and future outbreaks of EV-D68 viruses.

In an aspect, the disclosure provided methods for detection of enterovirus D68 in a sample. The method comprises: (a) contacting a nucleic acid obtained from the sample with an oligonucleotide primer comprising the sequence 5'-CACYGAACCAGARGAAGCCA-3' (SEQ ID NO:3) and an oligonucleotide primer comprising the sequence 3'-AARGAATCATCCCGTCGAAATC-5' (SEQ ID NO:4); (b) exposing the contacted sample to a DNA amplification process that provides for production of a 98 nucleotide amplification product of the enterovirus D68 VP1 gene; and (c) detecting the 98 nucleotide amplification product, wherein the presence of said amplification product indicates that the sample contained enterovirus D68.

In another aspect, the disclosure provides methods for detection of enterovirus D68 in a sample. The method comprises: (a) contacting a nucleic acid obtained from the sample with an oligonucleotide primer pair capable of annealing to a sequence contained with to residues 2475 to 2572 of the enterovirus D68 sequence of SEQ ID NO:1 and providing a DNA amplification product therefrom of at least about 50 nucleotides to 98 nucleotides in length; (b) exposing the contacted sample to a DNA amplification process that provides for production of a nucleotide amplification product of the enterovirus D68 VP1 gene; and (c) detecting the amplification product, wherein the presence of said amplification product indicates that the sample contained enterovirus D68.

In certain embodiments, one of the oligonucleotide primers will hybridize to residues 2475 to 2496 of SEQ ID NO:1.

In other embodiments, the nucleic acid is a cDNA obtained from the sample by subjecting RNA obtained from the sample to an RT-PCR process.

In different embodiments, the amplification product is detected with a probe that hybridizes to the amplification product.

In still other embodiments, the probe comprises the sequence 5'-TCGCACAGTGATAAATCAGCACGG-3' (SEQ ID NO:5) and at least one detectable label or a fluorescence emitting and a fluorescence quenching label.

In yet other embodiments, the amplification product comprises the sequence 5'-CACTGAACCAGAAGAAGC-CATACAAACTCGCACAGTGATAAATCAGCACGGTG-TATCCGAGACTCTAGTGGAGAATTTTCTCAGTAG AGCAGCTTTGG-3' (SEQ ID NO:6).

In certain embodiments, the amplification product is detected by a technique comprising annealing of a probe that is complementary to a strand of the amplification product.

The enterovirus D68 comprises the sequence set forth in GenBank Accession Number KM881710.2. Specifically, the enterovirus D68 sequence comprises the sequence set forth in

```
                                        SEQ ID NO: 1
(CCACTCCAAG GGCCCACGTG GCGGCTAGTA CTCTGGTACT

TCGGTACCTT TGTACGCCTG TTTTATCTCC CTTCCCAATG

TAACTTAGAA GTTCTTAAAT CAATGCTCAA TAGGTGGGGC

GCAAACCAGC GCTCTCATGA GCAAGCACTC CTGTCTCCCC

GGTGAGGTTG TATAAACTGT TCCCACGGTT GAAAACAACC

TATCCGTTAT CCGCTATAGT ACTTCGAGAA ACCTAGTACC

ACCTTTGGAT TGTTGACGCG TTGCGCTCAG CACACTAACC

CGTGTGTAGC TTGGGTCGAT GAGTCTGGAC ATACCTCACT

GGCGACAGTG GTCCAGGCTG CGTTGGCGGC CTACTCATGG

TGAAAGCCAT GAGACGCTAG ACATGAACAA GGTGTGAAGA

GTCTATTGAG CTACTATAGA GTCCTCCGGC CCCTGAATGC

GGCTAATCCT AACCATGGAG CAAGTGCTCA CAGGCCAGTG

AGTTGCTTGT CGTAATGCGC AAGTCCGTGG CGGAACCGAC

TACTTTGGGT GTCCGTGTTT CACTTTTTAC TTTTATGACT

GCTTATGGTG ACAATTTGAT ATTGTTACCA TTTAGCTTGT

CAAATCAATT GCAAAAGATC CTAAATCTTA TTTATCAACT

TGCATCTTGA TAACTTTAAT TTGAAAATTT TAACAATGGG

AGCTCAGGTT ACTAGACAAC AAACTGGCAC TCATGAAAAT

GCCAACATTG CCACAAATGG ATCTCATATC ACATACAATC
```

-continued

AGATAAACTT TTACAAGGAT AGCTATGCGG CTTCAGCCAG
CAAGCAGGAT TTTTCACAGG ACCCATCAAA ATTCACTGAA
CCAGTAGTGG AAGGTTTAAA AGCAGGGGCG CCAGTTTTGA
AATCTCCTAG TGCTGAGGCA TGTGGCTACA GTGATAGAGT
ATTACAGCTC AAATTAGGAA ATTCAGCTAT TGTCACCCAG
GAAGCAGCGA ACTACTGCTG CGCTTATGGT GAATGGCCCA
ATTACTTACC AGACCATGAA GCAGTAGCCA TTGATAAACC
TACACAACCA GAAACTGCTA CAGATAGATT CTACACTTTG
AAATCAGTCA AATGGGAAAC TGGAAGCACA GGATGGTGGT
GGAAACTACC CGATGCACTG AATAATATAG GCATGTTTGG
ACAGAATGTG CAGCATCACT ACCTATATAG ATCTGGTTTC
TTGATTCATG TGCAGTGTAA TGCCACAAAA TTCCATCAAG
GTGCCTTATT AGTGGTAGCA ATTCCAGAAC ATCAGAGGGG
AGCGCACAAC ACCAACACTA GCCCAGGGTT TGATGATATA
ATGAAAGGTG AAGAAGGAGG GACCTTCAAT CATCCATATG
TCCTTGATGA TGGAACATCA TTGGCTTGTG CGACGATATT
TCCACATCAG TGGATAAATC TGAGAACCAA CAATTCAGCA
ACAATTGTTC TTCCCTGGAT GAATGCTGCT CCAATGGATT
TCCCACTTAG ACATAATCAG TGGACGCTAG CAATAATACC
AGTGGTGCCA TTAGGTACGC GTACAACATC AAGTATGGTC
CCAATAACAG TTTCAATCGC TCCAATGTGT TGTGAGTTTA
ATGGACTTAG ACACGCCATT ACTCAAGGTG TCCCAACATA
CCTTTTACCA GGCTCGGGAC AATTCCTAAC AACTGATGAT
CATAGCTCTG CACCAGCTCT CCCGTGTTTC AACCCAACTC
CAGAAATGCA TATCCCAGGG CAGGTCCGTA ACATGCTAGA
AGTGGTCCAA GTGGAATCAA TGATGGAGAT TAATAACACA
GAAAGTGCAG TTGGCATGGA GCGTCTTAAG GTTGATATAT
CAGCATTGAC AGATGTCGAT CAATTGTTAT TCAACATTCC
ACTGGACATA CAGTTGGATG GGCCACTTAG AAACACTTTG
GTAGGAAACA TATCTAGATA TTACACTCAT TGGTCTGGAT
CCCTAGAAAT GACGTTTATG TTTTGTGGCA GCTTCATGGC
AACGGGAAAA TTAATCCTGT GCTATACTCC TCCAGGTGGA
TCATGCCCGA CAACCAGAGA GACCGCCATG TTAGGTACAC
ATATTGTTTG GGATTTTGGA TTACAATCTA GTGTAACCCT
GATAATACCT TGGATTAGTG GATCCCACTA CAGGATGTTT
AATAATGATG CTAAGTCAAC TAATGCCAAC GTTGGCTATG
TCACTTGTTT TATGCAGACC AATCTGATAG TCCCCAGTGA
ATCCTCTGAC ACGTGTTCCT TGATAGGGTT CATAGCAGCA
AAAGATGATT TCTCCCTCAG ATTAATGAGA GACAGCCCTG
ACATTGGACA ACTAGACCAT TTACATGCAG CAGAGGCAGC

-continued

CTACCAGATC GAGAGCATCA TCAAAACAGC GACCGACACT
GTGAAAAGTG AGATTAATGC TGAACTTGGT GTGGTCCCTA
GCTTAAATGC AGTTGAAACA GGTGCAACTT CTAACACTGA
ACCAGAAGAA GCCATACAAA CTCGCACAGT GATAAATCAG
CACGGTGTAT CCGAGACTCT AGTGGAGAAT TTTCTCAGTA
GAGCAGCTTT GGTATCAAAG AGAAGTTTTG AATACAAAGA
TCATACTTCG TCTGCAGCAC AAGCAGACAA GAACTTTTTC
AAATGGACAA TTAACACCAG ATCCTTTGTA CAGTTAAGAA
GAAAATTAGA ATTATTCACA TACCTTAGAT TTGATGCTGA
GATCACTATA CTCACAACTG TAGCAGTGAA TGGTAGTGGT
AATAATACAT ACGTGGGTCT TCCTGACTTG ACACTCCAAG
CAATGTTTGT ACCCACTGGT GCTCTTACCC CAGAAAAACA
GGACTCATTC CACTGGCAGT CAGGCAGTAA TGCTAGTGTA
TTCTTTAAAA TCTCCGACCC CCCAGCCAGA ATAACCATAC
CTTTTATGTG CATTAACTCA GCATACTCAG TTTTTATGA
TGGCTTTGCC GGATTTGAGA AAAACGGTCT GTATGGAATA
AATCCAGCTG ACACTATTGG TAACTTATGT GTTAGAATAG
TGAATGAACA CCAACCAGTT GGTTTCACAG TGACCGTTAG
GGTTTACATG AAGCCTAAAC ACATAAAAGC ATGGGCACCA
CGACCACCAC GAACTTTGCC ATATATGAGT ATTGCAAATG
CAAATTACAA AGGTAAAGAA AGAGCACCAA ATGCGCTCAA
TGCTATAATT GGCAATAGAG ACAGTGTCAA AACCATGCCT
CATAATATAG TGAACACTGG TCCAGGCTTC GGAGGAGTTT
TTGTAGGGTC TTTCAAAATA ATCAACTATC ACTTGGCCAC
TACAGAAGAG AGACAGTCAG CTATCTATGT GGATTGGCAA
TCAGACGTCT TGGTTACCCC CATTGCTGCT CATGGAAGGC
ACCAAATAGC AAGATGCAAG TGCAACACAG GGGTTTACTA
TTGTAGGCAC AAAAACAGAA GTTACCCGAT TTGCTTTGAA
GGCCCAGGGA TTCAATGGAT TGAACAAAAT GAATATTACC
CAGCAAGGTA CCAGACCAAT GTACTATTGG CAGTTGGTCC
TGCGGAAGCA GGAGATTGCG GTGGTTTACT AGTTTGTCCA
CATGGGGTAA TCGGTCTTCT TACAGCAGGA GGGGGTGGAA
TTGTAGCTTT CACTGATATC AGGAATTTGC TATGGTTAGA
TACTGATGCT ATGGAACAAG GCATTACTGA TTATATTCAA
AATCTTGGTA ATGCCTTTGG AGCAGGATTT ACAGAAACAA
TCTCTAATAA AGCCAAGGAA GTGCAAGATA TGCTAATTGG
AGAGAGTTCA CTATTAGAAA AATTGTTAAA AGCTCTAATC
AAAATCATAT CAGCATTAGT AATTGTAATC AGAAACTCAG
AAGATTTAGT CACAGTCACA GCCACACTAG CATTGTTGGG
ATGCCATGAT TCACCATGGA GCTACTTGAA ACAGAAGGTA
TGTTCATACT TAGGTATTCC TTATGTACCT AGACAGGGTG

-continued

AATCGTGGCT TAAGAAATTC ACAGAGGCAT GCAATGCTCT

TAGAGGTCTG GATTGGCTAT CGCAAAAGAT AGATAAATTC

ATCAACTGGC TTAAAACCAA AATATTACCA GAAGCTAGGG

AGAAATATGA ATTTGTGCAA AGGCTCAAAC AGTTACCGGT

GATAGAAAAC CAAGTTAGTA CAATCGAGCA TAGCTGCCCA

ACAACAGAAC AACAACAGGC CTTATTCAAC AACGTCCAAT

ACTATTCACA CTACTGTAGA AAGTACGCAC CACTTTACGC

AGTGGAAGCA AAGAGGGTAG TAGCTCTTGA AAAGAAAATA

AACAACTACA TCCAGTTCAA GTCCAAATCT CGCATTGAAC

CGGTTTGTTT AATAATACAT GGCTCTCCAG GAACTGGCAA

GTCAGTGGCT TCAAATTTAA TTGCCAGGGC TATCACAGAG

AAATTGGGGG GGGACATTTA TTCCTTGCCT CCAGACCCTA

AATATTTTGA TGGATACAAA CAGCAAACAG TGGTCCTCAT

GGATGATTTA ATGCAAAATC CAGATGGGAA TGACATATCT

ATGTTCTGCC AAATGGTCTC CACTGTAGAT TTCATACCCC

CAATGGCTAG TTTGGAGGAA AAAGGAACTC TATACACCAG

TCCATTTTTA ATAGCTACTA CCAATGCTGG CTCAATACAT

GCACCAACTG TATCAGACTC AAAGGCTTTG TCACGCAGAT

TTAAATTTGA CGTGGACATT GAAGTCACAG ATTCATACAA

GGACTCAAAT AAATTGGATA TGTCAAGGGC AGTCGAGATG

TGCAAACCAG ATGGCTGTGC CCCCACCAAT TACAAAAGAT

GCTGCCCATT GATCTGTGGA AAGGCTATCC AATTCAGAGA

TCGCAGAACT AATGCAAGAT CCACTATTGA TATGCTAGTA

ACTGATATTA TAAAGGAATA TAGAACCAGA AACAGTACAC

AGGATAAGCT GGAAGCTCTG TTTCAGGGGC CTCCACAGTT

TAAAGAGATC AAAATTTCAG TCACCCCAGA TACACCAGCT

CCTGATGCTA TAAATGACCT TCTTAGGTCA GTGGATTCTC

AAGAAGTTAG GGATTATTGC CAAAAGAAAG GATGGATTGT

AGTACACCCA TCAAATGAGC TAATAGTAGA AAAACACATT

AGTAGAGCTT TTATTACTCT ACAAGCCATT GCCACCTTTG

TATCAATAGC TGGTGTAGTT TATGTTATAT ACAAACTTTT

TGCTGGCATT CAGGGTCCAT ACACAGGAAT CCCCAATCCT

AAACCTAAAG TACCCTCTCT CAGAACAGCT AAAGTGCAAG

GACCAGGGTT CGATTTTGCA CAAGCCATAA TGAAGAAAAA

TACCGTCATT GCAAGGACTG AAAAGGGTGA GTTCACCATG

CTGGGTGTAT ATGATAGGGT AGCGGTCATC CCCACACACG

CATCTGTTGG AGAAACCATT TACATTAATG ATGTAGAGAC

TAAAGTTTTA GATGCGTGTG CACTTAGAGA CTTGACTGAT

ACAAACTTAG AGATAACCAT AGTCAAATTA GACCGTAATC

AAAAATTTAG AGATATCAGA CATTTTCTGC CCAGATATGA

-continued

GGATGATTAC AATGACGCTG TGCTTAGCGT ACATACATCA

AAATTCCCAA ATATGTATAT CCCAGTTGGA CAAGTCACCA

ATTATGGCTT CTTGAACCTA GGTGGTACAC CGACGCACCG

CATTTTAATG TATAACTTCC CAACAAGAGC TGGCCAGTGT

GGTGGTGTGG TGACAACTAC AGGTAAGGTG ATAGGAATAC

ATGTAGGTGG AAATGGAGCT CAAGGATTTG CAGCAATGCT

ACTACACTCT TACTTTTCCG ATACACAAGG TGAGATAGTT

AGTAGTGAAA AGAGTGGGGT GTGCATTAAC GCACCGGCAA

AGACTAAACT CCAACCTAGT GTTTTCCATC AAGTTTTTGA

AGGTTCAAAG GAACCAGCAG TTCTCAATCC AAAAGATCCT

AGGCTTAAAA CAGATTTCGA GGAGGCCATT TTCTCAAAGT

ACACAGGTAA CAAAATTATG TTAATGGATG AGTACATGGA

AGAGGCAGTG GATCATTATG TGGGGTGTTT AGAACCATTA

GACATCAGTG TGGATCCCAT ACCCCTGGAA AGTGCCATGT

ATGGAATGGA TGGCCTTGAG GCATTAGACT TAACTACCAG

TGCAGGATTC CCTTACTTAC TACAAGGGAA GAAGAAAAGG

GATATATTTA ATAGACATAC TAGAGACACC AGTGAAATGA

CAAAAATGTT AGAGAAATAT GGAGTTGACC TACCTTTTGT

AACCTTTGTA AAAGATGAGC TTAGATCAAG AGAAAAAGTT

GAAAAAGGGA AATCACGCCT GATTGAGGCC AGTTCCTTGA

ATGACTCAGT TGCTATGAGA GTTGCCTTTG GAAACCTTTA

CGCCACATTT CACAACAATC CAGGTACAGC AACTGGTAGT

GCAGTTGGTT GTGATCCAGA TATATTTTGG TCAAAAATCC

CTATTTTGTT AGATGGAGAA ATCTTTGCTT TTGACTACAC

TGGTTATGAT GCTAGTTTGT CACCAGTGTG GTTTGCCTGC

TTAAAGAAAG TTCTAATTAA GTTAGGTTAC ACACATCAAA

CGTCTTTTAT AGATTATTTG TGTCATTCAG TACATTTATA

TAAGGACAAA AAATACATAG TTAATGGTGG AATGCCCTCT

GGTTCTTCAG GCACCAGCAT ATTCAACACT ATGATCAACA

ATATAATCAT AAGAACTTTA TTAATTAGGG TTTACAAAGG

CATAGACCTG GACCAGTTCA AAATGATTGC CTATGGGGAT

GATGTTATTG CTAGCTACCC ACATAAGATT GATCCAGGTT

TGCTGGCAGA AGCAGGTAAA CAGTATGGAT TAGTAATGAC

GCCAGCAGAC AAAGGAACCA GTTTTATTGA CACAAATTGG

GAAAATGTAA CTTTCTTAAA AAGATATTTC AGAGCAGATG

ATCAATACCC CTTTCTCATA CATCCAGTGA TGCCAATGAA

AGAGATACAT GAATCTATTA GATGGACTAA AGATCCCAGA

AACACACAGG ATCATGTTAG GTCTTTGTGC TACCTCGCAT

GGCATAATGG AGAGGAGGCT TATAATGAAT TTGCAGAAAA

AATCAGAAGT GTGCCTGTGG GAAGAGCATT GACACTACCT

GCATACTCTA GTCTTAGACG GAAATGGTTA GATTCGTTCT

-continued

```
AGACAACTCT AATTGAAACC CAAGTTATAG TTACTTTCAT

TTAGAGGTAA ATTTTG).
```

The enterovirus D68 also codes for the polyprotein with GenBank Accession Number AIT18931.1. More specifically, the enterovirus D68 codes for the polyprotein comprising

```
                                            SEQ ID NO: 2
(MGAQVTRQQTGTHENANIATNGSHITYNQINFYKDSYAASASKQDFSQD

PSKFTEPVVEGLKAGAPVLKSPSAEACGYSDRVLQLKLGNSAIVTQEAAN

YCCAYGEWPNYLPDHEAVAIDKPTQPETATDRFYTLKSVKWETGSTGWWW

KLPDALNNIGMFGQNVQHHYLYRSGFLIHVQCNATKFHQGALLVVAIPEH

QRGAHNTNTSPGFDDIMKGEEGGTFNHPYVLDDGTSLACATIFPHQWINL

RTNNSATIVLPWMNAAPMDFPLRHNQWTLAIIPVVPLGTRTTSSMVPITV

SIAPMCCEFNGLRHAITQGVPTYLLPGSGQFLTTDDHSSAPALPCFNPTP

EMHIPGQVRNMLEVVQVESMMEINNTESAVGMERLKVDISALTDVDQLLF

NIPLDIQLDGPLRNTLVGNISRYYTHWSGSLEMTFMFCGSFMATGKLILC

YTPPGGSCPTTRETAMLGTHIVWDFGLQSSVTLIIPWISGSHYRMFNNDA

KSTNANVGYVTCFMQTNLIVPSESSDTCSLIGFIAAKDDFSLRLMRDSPD

IGQLDHLHAAEAAYQIESIIKTATDTVKSEINAELGVVPSLNAVETGATS

NTEPEEAIQTRTVINQHGVSETLVENFLSRAALVSKRSFEYKDHTSSAAQ

ADKNFFKWTINTRSFVQLRRKLELFTYLRFDAEITILTTVAVNGSGNNTY

VGLPDLTLQAMFVPTGALTPEKQDSFHWQSGSNASVFFKISDPPARITIP

FMCINSAYSVFYDGFAGFEKNGLYGINPADTIGNLCVRIVNEHQPVGFTV

TVRVYMKPKHIKAWAPRPPRTLPYMSIANANYKGKERAPNALNAIIGNRD

SVKTMPHNIVNTGPGFGGVFVGSFKIINYHLATTEERQSAIYVDWQSDVL

VTPIAAHGRHQIARCKCNTGVYYCRHKNRSYPICFEGPGIQWIEQNEYYP

ARYQTNVLLAVGPAEAGDCGGLLVCPHGVIGLLTAGGGGIVAFTDIRNLL

WLDTDAMEQGITDYIQNLGNAFGAGFTETISNKAKEVQDMLIGESSLLEK

LLKALIKIISALVIVIRNSEDLVTVTATLALLGCHDSPWSYLKQKVCSYL

GIPYVPRQGESWLKKFTEACNALRGLDWLSQKIDKFINWLKTKILPEARE

KYEFVQRLKQLPVIENQVSTIEHSCPTTEQQQALFNNVQYYSHYCRKYAP

LYAVEAKRVVALEKKINNYIQFKSKSRIEPVCLIIHGSPGTGKSVASNLI

ARAITEKLGGDIYSLPPDPKYFDGYKQQTVVLMDDLMQNPDGNDISMFCQ

MVSTVDFIPPMASLEEKGTLYTSPFLIATTNAGSIHAPTVSDSKALSRRF

KFDVDIEVTDSYKDSNKLDMSRAVEMCKPDGCAPTNYKRCCPLICGKAIQ

FRDRRTNARSTIDMLVTDIIKEYRTRNSTQDKLEALFQGPPQFKEIKISV

TPDTPAPDAINDLLRSVDSQEVRDYCQKKGWIVVHPSNELIVEKHISRAF

ITLQAIATFVSIAGVVYVIYKLFAGIQGPYTGIPNPKPKVPSLRTAKVQG

PGFDFAQAIMKKNTVIARTEKGEFTMLGVYDRVAVIPTHASVGETIYIND

VETKVLDACALRDLTDTNLEITIVKLDRNQKFRDIRHFLPRYEDDYNDAV

LSVHTSKFPNMYIPVGQVTNYGFLNLGGTPTHRILMYNFPTRAGQCGGVV
```

-continued

```
TTTGKVIGIHVGGNGAQGFAAMLLHSYFSDTQGEIVSSEKSGVCINAPAK

TKLQPSVFHQVFEGSKEPAVLNPKDPRLKTDFEEAIFSKYTGNKIMLMDE

YMEEAVDHYVGCLEPLDISVDPIPLESAMYGMDGLEALDLTTSAGFPYLL

QGKKKRDIFNRHTRDTSEMTKMLEKYGVDLPFVTFVKDELRSREKVEKGK

SRLIEASSLNDSVAMRVAFGNLYATFHNNPGTATGSAVGCDPDIFWSKIP

ILLDGEIFAFDYTGYDASLSPVWFACLKKVLIKLGYTHQTSFIDYLCHSV

HLYKDKKYIVNGGMPSGSSGTSIFNTMINNIIIRTLLIRVYKGIDLDQFK

MIAYGDDVIASYPHKIDPGLLAEAGKQYGLVMTPADKGTSFIDTNWENVT

FLKRYFRADDQYPFLIHPVMPMKEIHESIRWTKDPRNTQDHVRSLCYLAW

HNGEEAYNEFCRKIRSVPVGRALTLPAYSSLRRKWLDSF).
```

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Human enterovirus D68 (EV-D68) was first isolated from samples obtained in California in 1962 from four children with pneumonia and bronchiolitis (1). The type strain isolated from one of these children has been designated the Fermon strain. Subsequently, only small numbers of EV-D68 cases were reported until the early 2000s (2). However, from 2008-12 outbreaks in Japan, the Philippines, the Netherlands, and the USA (Georgia, Pennsylvania, and Arizona) have revealed EV-D68 as an emerging pathogen capable of causing severe respiratory illness (2-6). During the 2014 enterovirus/rhinovirus season in the United States, EV-D68 circulated at an unprecedented level (5). From August 2014 to January 2015, CDC and state public health laboratories confirmed a total of 1,153 cases of respiratory illness caused by EV-D68, with at least 14 deaths. Infected individuals were primarily children, and resided in 49 states and the District of Columbia (5). The CDC has also reported there were likely millions of EV-D68 infections in which the etiology was not determined (5).

In mid-August of 2014, hospitals in Missouri and Illinois noticed an increased number of patients with severe respiratory illness and reported the presence of EV-D68 (6). We also observed this pattern at St. Louis Children's Hospital in St. Louis, Mo. Because efforts to define the outbreak were hampered by the lack of a test for EV-D68 that did not require nucleotide sequencing, we undertook the development of a rapid, specific RT-PCR assay. We began by sequencing the genome of a representative EV-D68 isolate from St. Louis to obtain the sequence information required to define an assay with optimal sensitivity and specificity. EV-D68 causes respiratory illness (7) and the virus can be found in an infected person's respiratory secretions, such as saliva, nasal mucus, or sputum. Therefore, an appropriate assay would primarily focus on evaluating respiratory disease due to EV-D68 by targeting nasopharyngeal and other respiratory specimens.

Development goals for our EV-D68 RT-PCR assay included: 1) avoiding false-positive detection of closely related enteroviruses and rhinoviruses, 2) increasing sensitivity compared to other available assays, and 3) retaining capability for sensitive detection of all known EV-D68 variants.

Example 1. Comparison of WashU and CDC Assays

Figure 2:
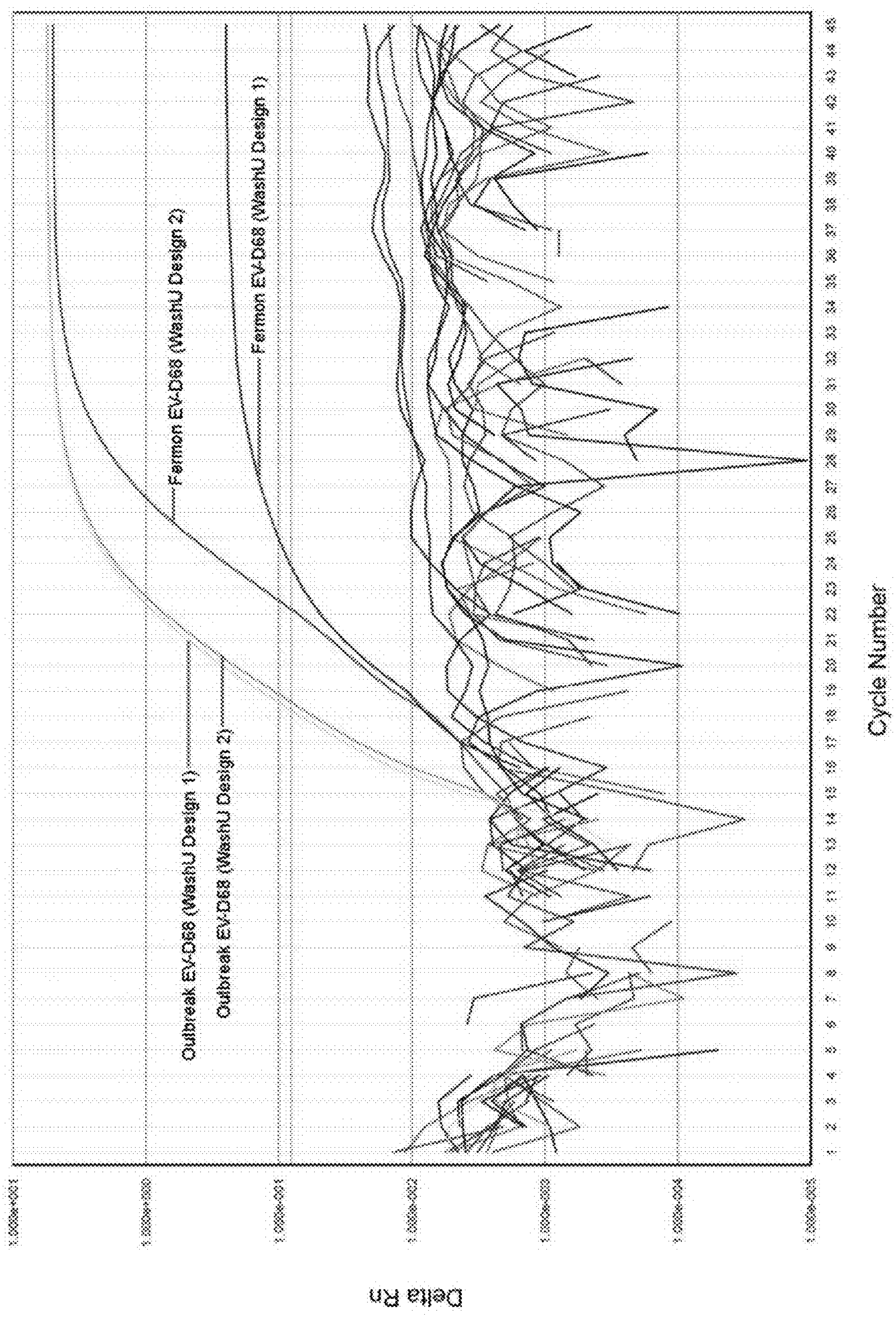
FIG. 2 depicts an amplification plot showing WashU RT-PCR assay EV-D68 sensitivity. PCR amplification cycle number is displayed on the Y-axis while log (ΔRn) is shown on the X-axis. Rn is the fluorescence of the reporter dye divided by the fluorescence of a passive reference dye. ΔRn is Rn minus the baseline and is plotted against PCR cycle number. The light green and light purple lines show detection of the 2014 EV-D68 outbreak strain using the WashU Design 1 and Design 2 assays, respectively. The brown and dark purple lines show detection of the more distant 1962 Fermon EV-D68 type-strain using the WashU Design 2 and Design 1 assays, respectively. The incorporation of degenerate bases and mixed primers in WashU Design 2 shows a significant increase in sensitivity (6.7 cycles earlier detection) for the Fermon type-strain (brown line), with minimal decrease in sensitivity to the 2014 outbreak strain (light purple) (<0.5 cycles difference).

We tested our two assays and the two versions of the CDC assay on a set of clinical samples from the 2014 outbreak (Table 2). We also included the Fermon strain of EV-D68 obtained from the University of Colorado. The two WashU assays performed similarly on the samples, with less than 1 cycle difference between the two assays for 12 of the 14 samples. The published CDC assay (FAM reporter) performed less well, failing to detect 6 of the 14 samples. However, modification of the fluorescent reporter on the CDC probe (i.e. substitution of FAM with Cy5) enabled detection of all 14 samples. However, the Ct values were higher for the modified CDC assay when compared to the WashU assays. The WashU assays but not the CDC assays detected the Fermon strain. Strikingly, the WashU Design 2 assay detected Fermon 6.7 RT-PCR cycles earlier than WashU Design 1 assay and the amplification curve indicated improved amplification efficiency (FIG. 2).

To follow-up on this observation, additional clinical samples from the 2014 season that had been tested with WashU Design 1 were identified for comparison with the modified CDC assay (Table 3). Only the modified assay was used because of its greater sensitivity. The samples were selected to include 10 from each of 4 categories based on the Ct of the WashU assay: Ct<22; Ct=2227; Ct=>27-32; Ct>32. Twenty samples negative for EV-D68 were also tested. In this test the CDC Cy5 assay detected all of the samples with Ct values <32, but failed to detect those with Ct values >32.

Example 2. Other EV-D68 Viruses

The WashU assays were used to test an additional 20 specimens positive for EV-D68 from the New York State Department of Health. Both WashU assays detected EV-D68 in each sample.

Example 3. Analysis of Specificity

Specificity of the WashU assays was evaluated using test panels provided by the New York State Department of Health, the University of Colorado, and our own Special Projects Laboratory. These panels included 4 different Coxsackie A viruses, 5 different Coxsackie B viruses, 9 different echoviruses, 3 enteroviruses including EV-D70, which is the enterovirus that is most closely related to EV-D68, and 59 rhinoviruses representing species A-C. All viruses tested are shown in Table 5. The presence of viral RNA was confirmed for each of these samples by amplification of the nucleic acid extract with an alternative pan-enterovirus/rhinovirus real-time RT-PCR assay. The WashU assays did not amplify any of the of the test panel viruses.

Example 4. Comparison with Laboratory-Developed and Commercial Assays

We compared sensitivity of the WashU EV-D68 assays with that of 5 commercial enterovirus assays and 2 LDTs (Table 4). We prepared 10-fold serial dilutions of a clinical sample from the 2014 St. Louis outbreak and tested each of the assays in parallel. We found that the WashU assays were able to detect EV-D68 at a dilution of $10^{-5}$, which was 10- to 100-fold more sensitive than the commercial Luminex xTag®, GenMark Dx eSensor®, Biofire FilmArray®, Cepheid GeneXpert®, and Focus Enterovirus assays. The LDT targeting the 5'-nontranslated region of EV-D68 showed equivalent sensitivity in detecting Fermon when compared to the WashU Design 2 assay; however, it had higher Ct values overall when compared to the WashU assays in detecting the 2014 outbreak strain, and was 10-fold less sensitive in serial dilution testing. Only the pan-enterovirus LDT had comparable sensitivity to the WashU assays.

Example 5. Analytic Sensitivity

In order to determine the limit of detection (LOD) of the WashU EV-D68 assay, the cloned 791-bp fragment of VP1 was serially diluted in a range of $6.25\times10^{0}$ to $5\times10^{5}$ copies per reaction and tested with the WashU Design 1 assay. Five replicates were carried out at each dilution. The resulting 95% LOD determined by probit regression analysis was 71 copies per reaction.

Discussion for the Examples

During the summer and fall of 2014, enterovirus D68 circulated at an unprecedented level in the United States (4-6). Because no molecular test was available for EV-D68-specific identification, laboratories were forced to rely on amplification and partial sequencing of the structural protein genes, VP4-VP2 or VP1 (16, 17), a much more cumbersome procedure than a specific real-time RT-PCR assay. The lack of a rapid molecular assay resulted in vast under-recognition and under-reporting of cases of EV-D68 infection because the majority of clinical laboratories did not have the ability to test specifically for EV-D68. Specific identification of EV-D68 was primarily from the CDC and state labs. Several FDA-approved multiplex assays for detection of respiratory viruses detect enteroviruses, but these systems are broadly reactive and do not distinguish between enteroviruses and rhinoviruses; results are typically reported as human rhinovirus/enterovirus.

In response to the 2014 nationwide enterovirus D68 outbreak and associated increase in severe respiratory illness presentations, we developed and evaluated a real-time reverse transcription PCR assay for detection of EV-D68 in clinical specimens. Development of this assay was informed by sequencing the complete genome of the EV-D68 virus circulating in St. Louis, Mo. during the outbreak. Our RT-PCR's primer and probe sequences were derived computationally by k-mer-mediated filtering of potentially cross-reactive, non-EV-D68 viral sequences. Broad detection of EV-D68 was achieved through multiple sequence alignment review using all published EV-D68 VP1 regions available through GenBank. Reduced sensitivity for the older, more distant Fermon EV-D68 type-strain, which has only 87.9% identity to the genome sequence of the St. Louis virus, led us to modify the assay, which then proved capable of efficiently amplifying more divergent EV-D68 viruses as well.

The CDC released the design and protocol for an EV-D68-specific RT-PCR on their website as a diagnostic resource for clinicians and health care professionals in mid-October 2014. As noted within the CDC's protocol, the amplicon size of 272 by is larger than ideal for a real-time RT-PCR assay. Furthermore, their selected TaqMan® probe had a guanine (G) at the 5'-end linked to the fluorophore FAM, potentially incurring unwanted fluorescence quenching. Replacement of FAM with Cy5 significantly improved the CDC assay's ability to detect EV-D68 in our tests (Table 2).

We evaluated the CDC's assay alongside our own, testing against EV-D68-positive clinical samples (n=35). Based on serial dilution testing of the 2014 outbreak virus, the WashU RT-PCR assays were 100-fold more sensitive than the published CDC assay, and the CDC assay failed to detect the Fermon strain. In addition, the WashU assays were at least 10-fold more sensitive for detection of EV-D68 than the FDA-approved commercial assays (i.e. Luminex xTAG RVP, GenMark Dx eSensor RVP, Biofire FilmArray IVD, and Cepheid GeneXpert) for enteroviruses/rhinoviruses detection (Table 4) with the further advantage of specific identification of EV-D68. The WashU assays showed no evidence of amplification of other enteroviruses, including the relatively closely related EV-D70 virus, or rhinoviruses.

Development of another EV-D68-specific RT-PCR by Piralla, et al. was communicated in March 2015 (24). This underscores the international interest in EV-D68 detection stimulated by the global reemergence of the virus in 2014. The assay targets a 60-bp region of the 5'-nontranslated region of EV-D68. Comparison of the assay to the CDC's RT-PCR and commercially available enterovirus/rhinovirus clinical assays was not reported. In our dilution tests, the assay was 10-fold less sensitive in detecting the 2014 outbreak strain of EV-D68 when compared to the WashU assays. Furthermore, the WashU assays detected the undiluted outbreak specimen 7 cycles before the 5'-nontranslated-targeting assay reached detection. Because these assays detect completely different segments of the viral genome, they may have complementary value in future applications.

While there are no specific treatments for EV-D68, and currently no antiviral targets available, rapid and accurate diagnosis of current and future EV-D68 infections is of great concern to clinicians and public health authorities. The EV-D68-specific RT-PCR assay we have developed can be used for epidemiological studies of the EV-D68 outbreak and for virus monitoring in subsequent seasons. Confirmation of EV-D68 infection is important for patient management, prognosis, reducing hospitalization, preventing outbreaks, and excluding other infectious diseases as causation (22). Furthermore, early and accurate diagnosis of this enterovirus can help control unnecessary antibiotic drug usage. Importantly, some FDA-approved multiplex respiratory panels may not optimally detect this virus. The ongoing importance of improved diagnostic capability for EV-D68 is underscored by the recent decision by the Department of Health and Human Services to encourage development of EV-D68 testing capability by authorizing emergency use of new in vitro diagnostics for EV-D68 detection (gpo.gov/fdsys/pkg/FR-2015-02-27/html/2015-04121.htm).

Methods for the Examples

Local specimens. After the EV-D68 outbreak was identified in August 2014 (6), clinical specimens testing positive for enterovirus/rhinovirus with the BioFire FilmArray Respiratory Virus Panel (BioFire Diagnostics, Inc., Salt Lake City, Utah) were provided for further testing by the Diagnostic Virology Laboratory at St. Louis Children's Hospital, consistent with a protocol for testing of de-identified residual clinical specimen material approved by the Washington University Human Research Protection Office. Fourteen enterovirus/rhinovirus-positive specimens were identified as containing EV-D68 by sequencing of the 5'-nontranslated region of each virus (8). Extracts of total nucleic acid were prepared from 100 μl aliquots of original specimen using a bioMerieux NucliSENS® easyMAG® automated extractor (bioMerieux Durham, N.C.).

Challenge panel from New York State Department of Health. We received a challenge panel from the New York State Department of Health (courtesy of Kirsten St. George and Daryl Lamson). Viruses included are shown in Table 5. This panel included nucleic acid extracts prepared using the NucliSENS® easyMAG® automated extractor from clinical specimens containing the following viruses, identified at the Wadsworth Laboratory by VP1 sequencing: Coxsackie A16 (n=2) and 21 (n=2), echovirus 18 (n=2) and 30, and enterovirus 71 (n=2). The panel also included a collection of 20 EV-D68 viruses selected to represent a range of sequence variants. A review of the VP1 sequences from this panel showed 93.8%-99.4% sequence identity when compared to the St. Louis 2014 strain. In comparison, the 1962 Fermon strain (see below) had 84.4% identity to the St. Louis 2014 strain in the sequenced VP1 region.

Challenge set from University of Colorado. We also received a challenge set from the University of Colorado (courtesy of Christine Robinson), consisting of frozen aliquots of cultures positive for the following viruses: Coxsackie A7 and 9; Coxsackie B 1-5; echoviruses 1,3,4,5,6, 11,19, and 30; and enteroviruses 68 (Fermon), 70, and 71. Most of these viruses were obtained originally from the American Type Culture Collection (ATCC®). Others were derived from clinical specimens that had been typed by the Centers for Disease Control (personal communication from Christine Robinson). All viruses received are shown in Table 5. Total nucleic acid extracts were prepared at Washington University.

Washington University samples. Our Special Projects Laboratory at Washington University provided an additional panel of challenge viruses. These viruses had been detected in patient specimens from research projects carried out in the past five years (9). Viruses in this panel had been typed based on sequencing a region of the 5'-nontranslated region (8). Total nucleic acid extracts were prepared using either the NucliSENS easyMAG automated extractor or Roche Magna Pure Compact System (Roche Diagnostics GmbH, Germany). Viruses included echovirus 14, Coxsackie A16, and 59 rhinoviruses from species A-C. The rhinovirus types and extraction methods are shown in Table 5.

EV-D68 St. Louis 2014 genome sequence. As previously described (10), we used high-throughput sequencing on the Illumina HiSeq 2500 to obtain one complete and eight partial sequences (GenBank: KM881710.2, BioProject: PRJNA263037) from specimens obtained during the 2014 outbreak in St. Louis. This genome sequence, along with other concurrently sequenced/published 2014 EV-D68 genomes, was used as a baseline for circulating EV-D68 sequence specificity.

PCR amplicon sequence selection. To create an assay with specificity for EV-D68, we performed comprehensive in silico analysis of all viruses in NIH's GenBank genetic sequence database using a k-mer approach described below to identify unique, contiguous sequences for candidate RT-PCR primers and probes. K-mer frequency-based methods were originally used in whole genome shotgun assembly algorithms to remove reads containing frequently occurring subsequences of length k during genome assembly (11, 12). We started by creating a consolidated viral sequence database by collecting all FASTA nucleotide sequences from viruses that infect vertebrate or invertebrate hosts, as found in the following areas of GenBank: RefSeq, Genome Neighbors, and Influenza Virus Resource. The database contained sequences from 34 viral families, which consisted of 190 annotated viral genera and 337 species. By design, this database contained only a single, complete EV-D68 reference genome (STL 2014 strain, GenBank: KM881710.2). Comprehensive k-mer analysis was performed on the database by indexing and reporting all 20-mer subsequences using Tallymer software (13). We eliminated 20-mers that were not unique in the k-mer pool, thus leaving 20-mers that were unique to EV-D68 as well as those unique to other viral species. EV-D68-unique 20-mers were collected by using BLAST (14) to align all unique 20-mers to the EV-D68 reference genome, requiring 100% identity. The EV-D68-specific 20-mers were consolidated into contiguous sequences by merging overlapping sequences with the BEDTools suite of utilities (15). Contiguous sequences ≥60 base pair (bp) were identified as promising regions for RT-PCR primer and probe design. Of these, a 141-bp region was selected based on its uniqueness, length, and relative conservation among available EV-D68 nucleotide sequences. Notably, this region was within the VP1 gene that is considered the "gold standard" for enterovirus typing (16, 17).

Design of oligonucleotide primers and probes. In addition to the VP1 gene sequence represented by our candidate 141-bp region from the St. Louis 2014 strain of EV-D68, we also collected 396 other unique EV-D68 VP1 sequences from GenBank. These nucleotide sequences were mapped and visualized online using MUSCLE (18) at the NIAID Virus Pathogen Database and Analysis Resource (ViPR) (viprbrc.org) website to produce a multiple sequence alignment (MSA). Focusing on the candidate 141-bp region within the MSA, we evaluated single nucleotide polymorphism (SNP) frequencies and identified conserved segments appropriate for primer and probe placement. The GenScript Real-time PCR Primer Design application (URL: genscript-.com/ssl-bin/app/primer) was used to evaluate primer/probe options. Criteria for ideal amplicon selection included: primer sequences no shorter than 20 bp, PCR amplicons <100 bp in length, and Tm values within a +55 to +70° C. range.

Figure 1B:
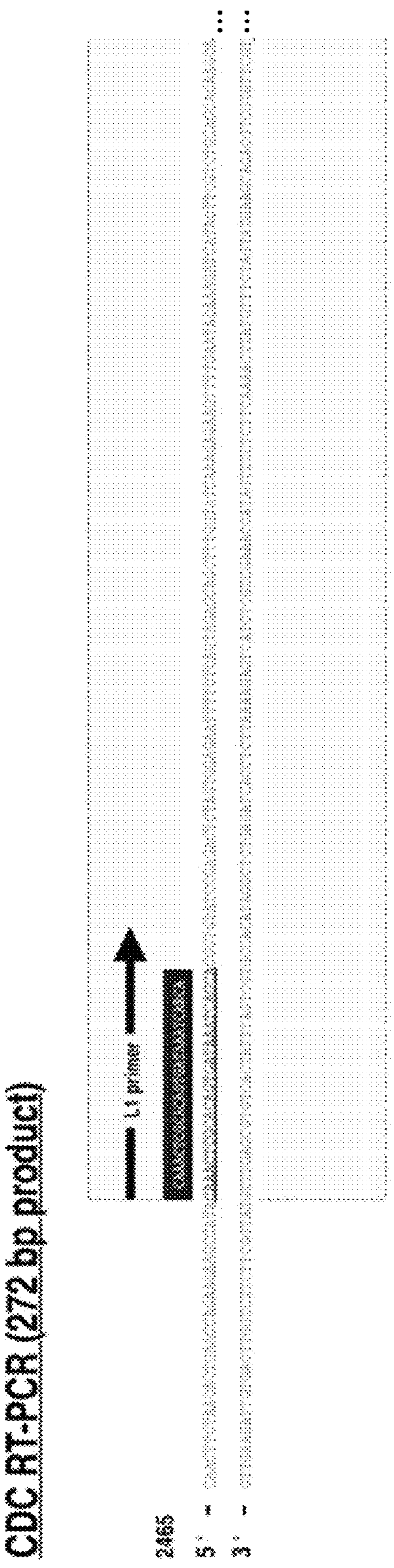
Figure 1C:
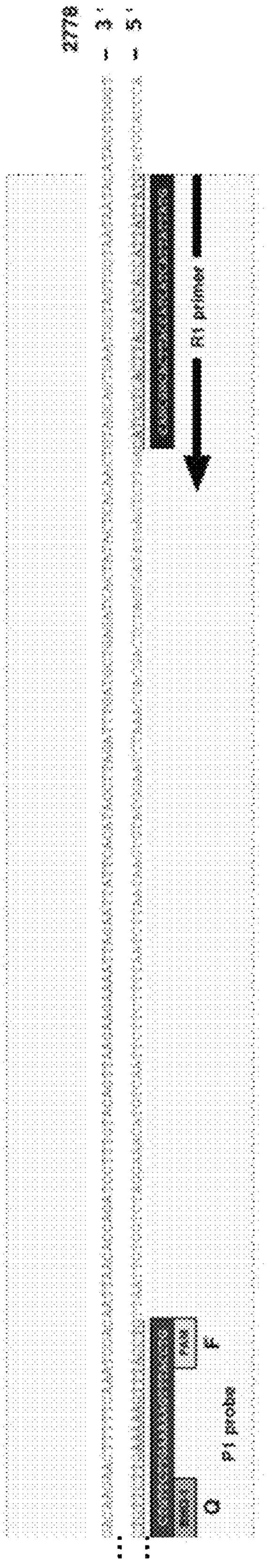

Based on this procedure, we selected an RT-PCR set consisting of two primers and a single probe with complete sequence identity to the 2014 outbreak virus (WashU Design 1). To broaden the detection of EV-D68 viruses, we made modifications based on SNP frequencies that included the addition of degenerate bases and a second reverse primer (WashU Design 2). Both designs are shown in Table 1 and FIG. 1.

Additional specificity analysis. The selected RT-PCR primer and probe sequences were aligned to GenBank nt database while excluding EV-D68 taxon (txid 42789) sequences, to evaluate possible homology to non-EV-D68 sequences. Using the NCBI's online BLAST interface (19, 20) for highly similar sequence alignment (megablast), fewer than 20 alignments (90-100% identity) were produced with all having identity to EV-D68 partial coding sequences that had been submitted to the database without full EV-D68 taxon designation (txid 1193974). Using discontiguous megablast, the top alignments that were not related to EV-D68 had between 70-83% sequence identity to EV-D70.

Washington University EV-D68 RT-PCR procedure. Primers and probes for the WashU assays were ordered from Applied Biosystems® at Life Technologies (Grand Island, N.Y.). Other reagents included low EDTA TE, Ag Path-ID One Step RT-PCR kit (Life Technologies), and $H_2O$ for negative controls. Master mixes consisting of 10× primer/probe (4 μM primers/2 μM probe) were produced for each assay and 20 μL of master mix was added to each well of a 96-well PCR plate. For the clinical specimens and controls, 5 μL of each sample was added to the reaction. ROX™ Passive Reference Dye was included in the RT-PCR buffer to normalize well-to-well differences. Reactions were run on the Applied Biosystems® 7500 Real-Time PCR System and analyzed using accompanying Ct (threshold cycle) analysis software. Thermal cycling conditions were: 45° C. for 10 minutes, followed by 95° C. for 10 minutes, followed by 45 cycles of 95° C. for 15 seconds and 60° C. for 45 seconds.

Modification of the CDC-published EV-D68 assay. In mid-October 2014, the CDC Picornavirus Laboratory made a new EV-D68-specific RT-PCR assay available (personal communication from Steve Oberste at the Centers for Disease Control and Prevention, Atlanta, Ga.). We tested the CDC EV-D68-specific RT-PCR according to the procedure available at that time on the CDC website. In addition, we tested the same assay with Cy5 replacing FAM as the probe reporter dye because of concerns for quenching of FAM by the guanine base located at the 5' end of the probe (21) (personal communication from Rangaraj Selvarangan, Children's Mercy Hospital, Kansas City, Mo.). Primers and probes for the CDC assay were ordered from Integrated DNA Technologies, Inc. (Coralville, Iowa).

Commercial and laboratory-developed assay testing. Commercial multiplex panels that detect enteroviruses/rhinoviruses were tested according to the manufacturers' instructions. These assays included: Luminex xTAG® Respiratory Viral Panel (Luminex, Austin, Tex.), GenMark Dx eSensor® Respiratory Viral Panel (GenMark Diagnostics, Inc., Carlsbad, Calif.), BioFire FilmArray® Respiratory Panel IVD (BioFire Diagnostics, Inc., Salt Lake City, Utah), Cepheid GeneXpert® EV IVD (Cepheid, Sunnyvale, Calif.), and Focus Enterovirus Primer Pair Analyte Specific Reagent (ASR) (Focus Diagnostics, Inc., Cypress, Calif.). We also evaluated two laboratory developed tests (LDTs), the pan-enterovirus assay described by Nijhuis, et al. (23) and an assay described by Piralla, et al. (24) that targets the 5'-non-translated region of EV-D68. To determine the relative sensitivities of the different LDTs and commercial molecular assays for the detection of EV68, material from the original specimen that yielded the full-length sequence of the St. Louis EV-D68 strain was used. For the Cepheid GeneXpert® and BioFire FilmArray® assays, which require raw un-extracted specimen, a series of 10-fold dilutions of the original specimen was made using Universal Transport Medium (UTM) (Diagnostic Hybrids, Athens, Ohio) as diluent. 300 μl of each dilution was then tested in the BioFire assay and 140 μl in the GeneXpert® assay according to the manufacturers' instructions. For the LDTs and the GeneMark and Luminex xTAG® assays, which require extracted nucleic acids, total nucleic acids were extracted from 100 μl of original specimen using a bioMerieux NucliSENS® easyMAG® automated extractor (bioMerieux Durham, N.C.). A series of 10-fold dilutions of the extract was then made using low EDTA TE as diluent, and each dilution was tested in each assay. For the Focus Enterovirus ASR assay, 5 μl of reaction mix and 5 μl of EasyMag nucleic acid extract was added to the wells of a 3MTM Integrated Cycler Universal Disc, and the amplification assay was run using standard Focus Diagnostics assay parameters and 3MTM Integrated Cycler. For the pan-enterovirus assay, we used the Ag Path-ID One Step RT-PCR kit and recommended cycling conditions, using an Applied Biosystems® 7500 Real-Time PCR System. For the assay targeting the 5'-nontranslated region of EV-D68, we followed the authors' recommended procedures and cycling conditions, using an Applied Biosystems® 7300 Real-Time PCR System.

Analytic limit of detection. A 791-bp region of VP1 containing the amplicon of the WashU assays was reverse transcribed, amplified and cloned from a clinical sample from the 2014 season from St. Louis using the primers EV68-VP1-2325-fwn GGRTTCATAGCAGCAAAAGATGA (SEQ ID NO:7) and EV68-VP1-3121-rvni TAGGYTTCATGTAAACCCTRACRGT (SEQ ID NO:8), which were previously described (23). The product was cloned using a TOPO® TA cloning kit (Life Technologies, Grand Island, N.Y.). Sequence was verified by dideoxy sequencing of the plasmid insert. The plasmid was linearized with Spel prior to its use as a template in the real-time RT-PCR assay. The analytic limit of detection (LOD) was determined by testing multiple replicates of dilutions of the linearized cloned VP1-containing plasmid. Probit analysis was carried out using the SAS (version 9.3 of the SAS system for Windows) software suite. As the Pearson Chi-Square was small (p>0.1000), fiducial limits were calculated using a z-value of 1.96.

REFERENCES FOR THE EXAMPLES

1. Schieble J H, Fox V L, Lennette E H. 1967. A probable new human picornavirus associated with respiratory diseases. American Journal of Epidemiology 85: 297-310.
2. Imamura T, Oshitani H. 2015. Global reemergence of enterovirus D68 as an important pathogen for acute respiratory infections. Rev. Med. Virol. 25:102-114.
3. Tokarz R, Firth C, Madhi S A, Stephen H, Wu W, Sall A, Haq S, Briese T, Lipkin I. 2012. Worldwide emergence of multiple clades of enterovirus 68. *The Journal of General Virology.* 93 (Pt 9): 1952-1958. doi:10.1099/vir.0.043935-0.
4. Morbidity and Mortality Weekly Report. Clusters of Acute Respiratory Illness Associated with Human Enterovirus 68—Asia, Europe, and United States, 2008-2010 (Sep. 30, 2011/60(38); 1301-1304). cdc.gov/mmwr/preview/mmwrhtml/mm6038a1.htm
5. Centers for Disease Control and Prevention. Enterovirus D68 in the United States, 2014. cdc.gov/non-polio-enterovirus/outbreaks/EV-D68-outbreaks.html
6. Morbidity and Mortality Weekly Report. Severe Respiratory Illness Associated with Enterovirus D68—Missouri and Illinois, 2014 (Sep. 12, 2014/63(36); 798-799). cdc.gov/mmwr/preview/mmwrhtml/mm6336a4.htm?s_cid=mm6336a4_w
7. Oberste M S, Maher K, Schnurr D, Flemister M R, Lovchik J C, Peters H, Sessions W, Kirk C, Chatterjee N, Fuller S, Hanauer J M, Pallansch M A. 2004. Enterovirus 68 is associated with respiratory illness and shares biological features with both the enteroviruses and the rhinoviruses. J. Gen. Virol. 85:2577-2584.
8. Lee W M, Kiesner C, Pappas T, Lee I, Grindle K, Jartti T, Jakiela B, Lemanske R F Jr, Shult P A, Gern J E. 2007. A diverse group of previously unrecognized human rhinoviruses are common causes of respiratory illnesses in infants. PLoS One. 2(10):e966.
9. Colvin J M, Muenzer J T, Jaffe D M, Smason A, Deych E, Shannon W D, Arens M Q, Buller R S, Lee W M, Weinstock E J, Weinstock G M, Storch G A. 2012. Detection of viruses in young children with fever without an apparent source. Pediatrics. 130(6):e1455-62.
10. Wylie K M, Wylie T N, Orvedahl A, Buller R S, Herter B N, Magrini V, Wilson R K, Storch G A. 2015. Genome sequence of enterovirus D68 from St. Louis, Mo., USA. Emerging Infect. Dis. 21:184-186.
11. Sutton G, White 0, Adams M, Kerlavage A. 1995. TIGR Assembler: a new tool for assembling large shotgun sequencing projects. Genome Sci Technol 1:9-19.
12. Huson D H, Reinert K, Kravitz S A, Remington K A, Delcher A L, Dew I M, Flanigan M, Halpern A L, Lai Z, Mobarry C M, Sutton G G, Myers E W. 2001. Design of a compartmentalized shotgun assembler for the human genome. Bioinformatics 17(Suppl 1):S132-9.
13. Kurtz S, Narechania A, Stein J C, Ware D. 2008. A new method to compute K-mer frequencies and its application to annotate large repetitive plant genomes. BMC Genomics 9:517.
14. Altschul S F, Gish W, Miller W, Myers E W, Lipman D J. 1990. Basic local alignment search tool. J. Mol. Biol. 215:403-410.
15. Quinlan A R, Hall I M. 2010. BEDTools: a flexible suite of utilities for comparing genomic features. Bioinformatics 26:841-842.
16. Oberste M S, Maher K, Kilpatrick D R, Flemister M R, Brown B A, Pallansch M A. 1999. Typing of Human Enteroviruses by Partial Sequencing of VP1 1-6. J Clin Microbiol. 37(5):1288-93.
17. Nix W A, Oberste M S, Pallansch M A. 2006. Sensitive, seminested PCR amplification of VP1 sequences for direct identification of all enterovirus serotypes from original clinical specimens. J. Clin. Microbiol. 44:2698-2704.
18. Edgar R C. 2004. MUSCLE: multiple sequence alignment with high accuracy and high throughput. Nucleic Acids Res. 32:1792-1797.
19. Johnson M, Zaretskaya I, Raytselis Y, Merezhuk Y, McGinnis S, Madden T L. 2008. NCBI BLAST: a better web interface. Nucleic Acids Res. 36:W5-9.
20. Boratyn G M, Camacho C, Cooper P S, Coulouris G, Fong A, Ma N, Madden T L, Matten W T, McGinnis S D, Merezhuk Y, Raytselis Y, Sayers E W, Tao T, Ye J, Zaretskaya I. 2013. BLAST: a more efficient report with usability improvements. Nucleic Acids Res. 41:W29-33.
21. Xiao M, Kwok P-Y. 2003. DNA analysis by fluorescence quenching detection. Genome Res. 13:932-939.
22. Nijhuis M, van Maarseveen N, Schuurman R, Verkuijlen S, de Vos M, Hendriksen K, van Loon A M. 2002. Rapid and Sensitive Routine Detection of All Members of the Genus Enterovirus in Different Clinical Specimens by Real-Time PCR. J. Clin. Microbiol. 40:3666-3670.
23. Rahamat-Langendoen J, Riezebos-Brilman A, Borger R, van der Heide R, Brandenburg A, Scholvinck E, Niesters H G M. 2011. Upsurge of human enterovirus 68 infections in patients with severe respiratory tract infections. J. Clin. Virol. 52:103-106.
24. Piralla A, Girello A, Premoli M, Baldanti F. 2015. A new Real-Time RT-PCR Assay for Detection of Human Enterovirus 68 (EV-D68) in Respiratory Samples. J. Clin. Microbiol. J C M.03691-14.

TABLE 1

| WashU EV-D68-specific RT-PCR assay primers and probes | | | | | | |
|---|---|---|---|---|---|---|
| Designation | ID | Sequence (5'-3') | Strand | Location[c] | Tm | Mod. |
| WashU Design 1[a] | L1-1 | CACTGAACCAGAAGAAGCCA (SEQ ID NO: 9) | forward | 2475-2494 | 59.01 | n/a |
| WashU Design 1[a] | R1-1 | CCAAAGCTGCTCTACTGAGAAA (SEQ ID NO: 10) | reverse | 2551-2572 | 58.93 | n/a |
| WashU Design 1[a] | P1-1 | TCGCACAGTGATAAATCAGCACGG (SEQ ID NO: 5) | forward | 2502-2525 | 68.39 | 5' Fam & 3' Tamra |
| WashU Design 2[b] | L1-2 | CACYGAACCAGARGAAGCCA (SEQ ID NO: 3) | forward | 2475-2494 | 58.38-59.01* | n/a |
| WashU Design 2[b] | R1-2 | CCAAAGCTGCTCTACTGAGAAA (SEQ ID NO: 10) | reverse | 2551-2572 | 58.10-59.75* | n/a |
| WashU Design 2[b] | R2-2 | CTAAAGCTGCCCTACTAAGRAA (SEQ ID NO: 11) | reverse | 2551-2572 | 58.10-59.75* | n/a |
| WashU Design 2[b] | P1-2 | TCGCACAGTGATAAATCAGCAYGG (SEQ ID NO: 12) | forward | 2502-2525 | 68.39-69.21* | 5' Fam & 3' Tamra |

Y = T, C; R = G, A
n/a: not applicable
[a]Distinct, single paired-primer design. Amplicon size is 98 bp.
[b]Degenerate bases and mixed primers included in design. Amplicon size is 98 bp.
[c]EV-D68 STL 2014 (GenBank: KM881710.2) subregion positions, 5'-3' orientation.
*Tm ranges span all combinations of degenerate bases and mixed primers.

TABLE 2

| Comparisons of WashU and CDC assays | | | | | | |
|---|---|---|---|---|---|---|
| | Ct values: | | | | ΔCt: | |
| Test Material | WashU Design 1[a] | WashU Design 2[b] | CDC[c] | Modified CDC[d] | WashU Design 1[a] and WashU Design 2[b] | WashU Design 2[b] and Modified CDC |
| EV-D68 specimens: | | | | | | |
| WU-EV-1 | 21 | 21.3 | neg | 23.7 | 0.3‡ | 2.4 |
| WU-EV-2 | 24.2 | 25.4 | neg | 28.7 | 1.2 | 3.3 |
| WU-EV-3 | 20 | 20.7 | 41 | 22.7 | 0.8 | 1.9 |
| WU-EV-4 | 20.7 | 20.8 | neg | 22.5 | 0.1‡ | 1.7 |
| WU-EV-5 | 22.2 | 22.7 | 34.6 | 24.4 | 0.5‡ | 1.7 |
| WU-EV-6 | 20.9 | 21.2 | 25.9 | 23.9 | 0.3‡ | 2.7 |
| WU-EV-7 | 20.5 | 20 | neg | 23.4 | −0.5‡ | 3.4 |
| WU-EV-8 | 27.3 | 27.3 | neg | 30.8 | 0‡ | 3.5 |
| WU-EV-9 | 17.3 | 17.5 | 27.7 | 20.5 | 0.2‡ | 3 |
| WU-EV-10 | 21.4 | 22.1 | 37.2 | 23.8 | 0.7 | 1.7 |
| WU-EV-11 | 26.3 | 26.8 | neg | 30.8 | 0.5‡ | 4.1 |
| WU-EV-12 | 24.1 | 24.5 | 38.5 | 27.5 | 0.4‡ | 3.1 |
| WU-EV-13 | 11.2 | 11 | 23.9 | 14.7 | −0.2‡ | 3.7 |
| WU-EV-14 | 20.3 | 18.5 | 32.7 | 20.6 | −1.7‡ | 2.1 |
| Fermon | 22.7 | 15.9 | neg | neg | −6.7‡ | n/a |
| water | neg | neg | neg | neg | n/a | n/a |

Ct: Crossing threshold;
n/a: not applicable
[a]Distinct, single paired-primer design.
[b]Degenerate bases and mixed primers included in design.
[c]CDC published design with FAM.
[d]Modification of CDC assay by replacement of FAM with Cy5.
‡ΔCt <= 0.5

TABLE 3

| Comparison of WashU Design 1 and modified CDC assays applied to clinical samples | | | |
|---|---|---|---|
| | | Positive tests: | |
| Ct value range (WashU Design 1 defined) | # Samples tested | WashU Design 1 | Modified CDC |
| <22 | 10 | 10 | 10 |
| 22-27 | 10 | 10 | 10 |
| >27-32 | 10 | 10 | 10 |
| >32 | 10 | 10 | 0 |
| neg | 20 | 20 | 20 |

TABLE 4

Comparison of laboratory-developed and commercial assays

| | Laboratory-developed assays: | | | | | Commercial assays: | | | | |
|---|---|---|---|---|---|---|---|---|---|---|
| Test Material | WashU Design 1[a] | WashU Design 2[a] | Modified CDC[a] | 5'-non-translated[a,b] | Pan-entero[a,c] | Luminex xTAG RVP[d] | Gen-Mark Dxe Sensor RVP[e] | Biofire Film-Array IVD | Cepheid Gene-Xpert[a] | Focus Entero-virus ASR[a] |
| EV-D68[‡] dilutions: | | | | | | | | | | |
| $10^{-1}$ | 21.3 | 22.9 | 23.5 | 30.0 | 27.1 | 4415 | 10.5 | pos | 28.1 | 28.2 |
| $10^{-2}$ | 24.0 | 25.5 | 28.0 | 33.0 | 30.1 | 5112 | 3.4 | pos | 31.2 | 31.6 |
| $10^{-3}$ | 28.5 | 29.9 | 34.2 | 36.1 | 33.7 | 5405 | 6.9 | pos | 34.1 | 35.9 |
| $10^{-4}$ | 31.8 | 33.1 | neg | 41.0 | 38.1 | 1132 | neg | pos | neg | 38.1 |
| $10^{-5}$ | 36.2 | 37.0 | neg | neg | 37.1 | neg | neg | neg | nt | neg |
| $10^{-6}$ | neg | neg | neg | neg | neg | neg | neg | neg | nt | neg |
| Fermon* | 20.0 | 15.4 | neg | 15.2 | 18.5 | 4775 | neg | nt | nt | 20.7 |
| EV-D70* | neg | neg | neg | neg | 14.5 | 3023 | 6.8 | nt | nt | 13.7 |
| water | neg | neg | neg | neg | neg | neg | nt | nt | nt | neg |

nt = not tested

[a]Ct (cross threshold) values.

[b]Protocol as described by Piralla, et al.

[c]Protocol as described by Nijhuis, et al. Modifications described in Methods.

[d]Luminex MFI (Mean Fluorescence Index) values: negative <150; equivocal 150-300; positive >300.

[e]GenMark nanoampere (nA) values: positve >3 with >100 being strong postive.

[‡]Nucleic acid extracted from nasopharyngeal swab from EV-D68-positive patient. See Methods section for details.

*ATTC ® strains; total nucleic acid extracted from infected cell culture.

TABLE 5

Enteroviruses and rhinoviruses tested for cross-reativity with WashU RT-PCR assays

| ID | Entero / Rhino | Type | Extraction | Source |
|---|---|---|---|---|
| WU-ER-1* | Rhinovirus | W45 (HRVC) | NucliSENS easyMAG | St. Louis Children's Hospital |
| WU-ER-2* | Rhinovirus | W11 (HRVC) | NucliSENS easyMAG | St. Louis Children's Hospital |
| WU-ER-3* | Rhinovirus | W47 (HRVC) | NucliSENS easyMAG | St. Louis Children's Hospital |
| WU-ER-4* | Rhinovirus | R16 (HRVA) | NucliSENS easyMAG | St. Louis Children's Hospital |
| WU-ER-5* | Rhinovirus | R80 (HRVA) | NucliSENS easyMAG | St. Louis Children's Hospital |
| WU-ER-6* | Rhinovirus | R76 (HRVA) | NucliSENS easyMAG | St. Louis Children's Hospital |
| WU-ER-7* | Rhinovirus | R38 (HRVA) | NucliSENS easyMAG | St. Louis Children's Hospital |
| WU-ER-8* | Rhinovirus | R76 (HRVA) | NucliSENS easyMAG | St. Louis Children's Hospital |
| WU-ER-9* | Rhinovirus | R6 (HRVB) | NucliSENS easyMAG | St. Louis Children's Hospital |
| WU-ER-10* | Rhinovirus | R69 (HRVB) | NucliSENS easyMAG | St. Louis Children's Hospital |
| WU-ER-11* | Rhinovirus | W20 (HRVC) | NucliSENS easyMAG | St. Louis Children's Hospital |
| WU-ER-12* | Rhinovirus | W36 (HRVC) | NucliSENS easyMAG | St. Louis Children's Hospital |
| WU-ER-13* | Rhinovirus | R4 (HRVB) | NucliSENS easyMAG | St. Louis Children's Hospital |
| WU-ER-14* | Rhinovirus | W38 (HRVC) | NucliSENS easyMAG | St. Louis Children's Hospital |
| WU-ER-15* | Rhinovirus | W24 (HRVC) | NucliSENS easyMAG | St. Louis Children's Hospital |
| WU-ER-16* | Rhinovirus | R3 (HRVB) | NucliSENS easyMAG | St. Louis Children's Hospital |
| WU-ER-17* | Rhinovirus | R80 (HRVA) | NucliSENS easyMAG | St. Louis Children's Hospital |
| WU-ER-18* | Rhinovirus | R026 (HRVC) | NucliSENS easyMAG | St. Louis Children's Hospital |
| WU-ER-19* | Rhinovirus | R83 (HRVB) | NucliSENS easyMAG | St. Louis Children's Hospital |
| WU-ER-20* | Rhinovirus | R5 (HRVA) | NucliSENS easyMAG | St. Louis Children's Hospital |
| WU-ER-21* | Rhinovirus | R45 (HRVB) | NucliSENS easyMAG | St. Louis Children's Hospital |
| WU-ER-22* | Rhinovirus | W36 (HRVC) | NucliSENS easyMAG | St. Louis Children's Hospital |
| WU-ER-23* | Enterovirus | CVA16 | NucliSENS easyMAG | St. Louis Children's Hospital |
| WU-ER-24* | Enterovirus | ECHO14 | NucliSENS easyMAG | St. Louis Children's Hospital |
| WU-ER-25[‡] | Rhinovirus | R33 (HRVA) | Roche Magna Pure Compact | St. Louis Children's Hospital |

TABLE 5-continued

Enteroviruses and rhinoviruses tested for cross-reativity with WashU RT-PCR assays

| ID | Entero / Rhino | Type | Extraction | Source |
|---|---|---|---|---|
| WU-ER-26‡ | Rhinovirus | R29/R44 (HRVA) | Roche Magna Pure Compact | St. Louis Children's Hospital |
| WU-ER-27‡ | Rhinovirus | R46 (HRVA) | Roche Magna Pure Compact | St. Louis Children's Hospital |
| WU-ER-28‡ | Rhinovirus | W10 (HRVC) | Roche Magna Pure Compact | St. Louis Children's Hospital |
| WU-ER-29‡ | Rhinovirus | R52 (HRVB) | Roche Magna Pure Compact | St. Louis Children's Hospital |
| WU-ER-30‡ | Rhinovirus | W33 (HRVC) | Roche Magna Pure Compact | St. Louis Children's Hospital |
| WU-ER-31‡ | Rhinovirus | W46 (HRVC) | Roche Magna Pure Compact | St. Louis Children's Hospital |
| WU-ER-32‡ | Rhinovirus | R81 (HRVA) | Roche Magna Pure Compact | St. Louis Children's Hospital |
| WU-ER-33‡ | Rhinovirus | R60 (HRVA) | Roche Magna Pure Compact | St. Louis Children's Hospital |
| WU-ER-34‡ | Rhinovirus | R15 (HRVA) | Roche Magna Pure Compact | St. Louis Children's Hospital |
| WU-ER-35‡ | Rhinovirus | R68 (HRVA) | Roche Magna Pure Compact | St. Louis Children's Hospital |
| WU-ER-36‡ | Rhinovirus | R14 HRVB) | Roche Magna Pure Compact | St. Louis Children's Hospital |
| WU-ER-37‡ | Rhinovirus | W50 (HRVC) | Roche Magna Pure Compact | St. Louis Children's Hospital |
| WU-ER-38‡ | Rhinovirus | R3 (HRVB) | Roche Magna Pure Compact | St. Louis Children's Hospital |
| WU-ER-39‡ | Rhinovirus | R83 (HRVB) | Roche Magna Pure Compact | St. Louis Children's Hospital |
| WU-ER-40‡ | Rhinovirus | R25 (HRVA) | Roche Magna Pure Compact | St. Louis Children's Hospital |
| WU-ER-41‡ | Rhinovirus | W24 (HRVC) | Roche Magna Pure Compact | St. Louis Children's Hospital |
| WU-ER-42‡ | Rhinovirus | R22 (HRVA) | Roche Magna Pure Compact | St. Louis Children's Hospital |
| WU-ER-43‡ | Rhinovirus | W41 (HRVC) | Roche Magna Pure Compact | St. Louis Children's Hospital |
| WU-ER-44‡ | Rhinovirus | W6 (HRVC) | Roche Magna Pure Compact | St. Louis Children's Hospital |
| WU-ER-45‡ | Rhinovirus | W4 (HRVC) | Roche Magna Pure Compact | St. Louis Children's Hospital |
| WU-ER-46‡ | Rhinovirus | R10 (HRVA) | Roche Magna Pure Compact | St. Louis Children's Hospital |
| WU-ER-47‡ | Rhinovirus | R49 (HRVA) | Roche Magna Pure Compact | St. Louis Children's Hospital |
| WU-ER-48‡ | Rhinovirus | R61 (HRVA) | Roche Magna Pure Compact | St. Louis Children's Hospital |
| WU-ER-49‡ | Rhinovirus | R97 (HRVB) | Roche Magna Pure Compact | St. Louis Children's Hospital |
| WU-ER-50‡ | Rhinovirus | R58 (HRVA) | Roche Magna Pure Compact | St. Louis Children's Hospital |
| WU-ER-51‡ | Rhinovirus | R82 (HRVA) | Roche Magna Pure Compact | St. Louis Children's Hospital |
| WU-ER-52‡ | Rhinovirus | R21 (HRVA) | Roche Magna Pure Compact | St. Louis Children's Hospital |
| WU-ER-53‡ | Rhinovirus | R12 (HRVA) | Roche Magna Pure Compact | St. Louis Children's Hospital |
| WU-ER-54‡ | Rhinovirus | R53 (HRVA) | Roche Magna Pure Compact | St. Louis Children's Hospital |
| WU-ER-55‡ | Rhinovirus | R41 (HRVA) | Roche Magna Pure Compact | St. Louis Children's Hospital |
| WU-ER-56‡ | Rhinovirus | R1B (HRVA) | Roche Magna Pure Compact | St. Louis Children's Hospital |
| WU-ER-57‡ | Rhinovirus | R9 (HRVA) | Roche Magna Pure Compact | St. Louis Children's Hospital |
| WU-ER-58‡ | Rhinovirus | R11 (HRVA) | Roche Magna Pure Compact | St. Louis Children's Hospital |
| WU-ER-59‡ | Rhinovirus | R2 (HRVA) | Roche Magna Pure Compact | St. Louis Children's Hospital |
| WU-ER-60‡ | Rhinovirus | R27 (HRVB) | Roche Magna Pure Compact | St. Louis Children's Hospital |
| WU-ER-61‡ | Rhinovirus | W32 (HRVC) | Roche Magna Pure Compact | St. Louis Children's Hospital |
| WU-ER-62 | Enterovirus | CVA7 (AB-IV) | NucliSENS easyMAG | Children's Hospital Colorado |
| WU-ER-63 | Enterovirus | EV71 (wild) | NucliSENS easyMAG | Children's Hospital Colorado |
| WU-ER-64 | Enterovirus | CVB5 (Faulkner) | NucliSENS easyMAG | Children's Hospital Colorado |
| WU-ER-65 | Enterovirus | ECHO 19 (Burke) | NucliSENS easyMAG | Children's Hospital Colorado |
| WU-ER-66 | Enterovirus | CVA9 (PB/Bozek) | NucliSENS easyMAG | Children's Hospital Colorado |
| WU-ER-67 | Enterovirus | CVB2 (LLC-MK2) | NucliSENS easyMAG | Children's Hospital Colorado |
| WU-ER-68 | Enterovirus | ECHO 11 (Gregory) | NucliSENS easyMAG | Children's Hospital Colorado |
| WU-ER-69 | Enterovirus | ECHO 30 (wild) | NucliSENS easyMAG | Children's Hospital Colorado |
| WU-ER-70 | Enterovirus | CVB3 (wild) | NucliSENS easyMAG | Children's Hospital Colorado |
| WU-ER-71 | Enterovirus | CVB1 (Conn-5) | NucliSENS easyMAG | Children's Hospital Colorado |
| WU-ER-72 | Enterovirus | CVB4 (JVB) | NucliSENS easyMAG | Children's Hospital Colorado |
| WU-ER-73 | Enterovirus | ECHO 3 (Morrisey) | NucliSENS easyMAG | Children's Hospital Colorado |
| WU-ER-74 | Enterovirus | ECHO 6 (DiAmori) | NucliSENS easyMAG | Children's Hospital Colorado |
| WU-ER-75 | Enterovirus | ECHO 4 (wild) | NucliSENS easyMAG | Children's Hospital Colorado |
| WU-ER-76 | Enterovirus | ECHO 5 (wild) | NucliSENS easyMAG | Children's Hospital Colorado |
| WU-ER-77 | Enterovirus | ECHO 1 (Farouk) | NucliSENS easyMAG | Children's Hospital Colorado |
| WU-ER-78 | Enterovirus | EV70 (J670/71) | NucliSENS easyMAG | Children's Hospital Colorado |
| WU-ER-79 | Enterovirus | ECHO 7 | NucliSENS easyMAG | Children's Hospital Colorado |
| WU-ER-80 | Enterovirus | EV2 (Cox A16 Group A) | NucliSENS easyMAG | New York State Department of Health |
| WU-ER-81 | Enterovirus | EV3 (Echo 18 Group B) | NucliSENS easyMAG | New York State Department of Health |
| WU-ER-82 | Enterovirus | EV4 (Cox A21 Group C) | NucliSENS easyMAG | New York State Department of Health |
| WU-ER-83 | Enterovirus | EV5 (Echo 30 Group B) | NucliSENS easyMAG | New York State Department of Health |
| WU-ER-84 | Enterovirus | EV6 (Cox A21 Group C) | NucliSENS easyMAG | New York State Department of Health |
| WU-ER-85 | Enterovirus | EV7 (Echo 18 Group B) | NucliSENS easyMAG | New York State Department of Health |
| WU-ER-86 | Enterovirus | EV10 (Entero 71 Group A) | NucliSENS easyMAG | New York State Department of Health |
| WU-ER-87 | Enterovirus | EV11 (Cox A16 Group A) | NucliSENS easyMAG | New York State Department of Health |
| WU-ER-88 | Enterovirus | EV21 (Entero 71 Group A) | NucliSENS easyMAG | New York State Department of Health |

CVA: Coxsackie A virus;
CVB: Coxsackie B virus;
ECHO: echovirus;
EV: enterovirus
*Specimen collection funded by NIAID grant number R01AI097213.
‡Specimen collection funded by NIAID grant number U01AI077810.

What is claimed is:

1. A method for detection of enterovirus D68 in a sample, the method comprising:

a) contacting a nucleic acid obtained from the sample with an oligonucleotide primer consisting essentially of the sequence 5'-CACYGAACCAGARGAAGCCA-3' (SEQ ID NO:3) and an oligonucleotide primer consisting essentially of the sequence 3'-AARGAATCATCCCGTCGAAATC-5' (SEQ ID NO:4);

b) exposing the contacted sample to a DNA amplification process that provides for production of a 98 nucleotide amplification product of the enterovirus D68 VP1 gene; and c) detecting the 98 nucleotide amplification product, wherein the presence of said amplification product indicates that the sample contained enterovirus D68.

2. The method of claim 1, wherein one of the oligonucleotide primers hybridizes to residues 2475 to 2496 of SEQ ID NO:1.

3. The method of claim 1, wherein the nucleic acid is a cDNA obtained from the sample by subjecting RNA obtained from the sample to an RT-PCR process.

4. The method of claim 1, wherein the amplification product is detected with a probe that hybridizes to the amplification product.

5. The method of claim 4, wherein the probe comprises the sequence 5'-TCGCACAGTGATAAATCAGCACGG-3' (SEQ ID NO:5) and at least one detectable label.

6. The method of claim 1, wherein the amplification product consists of the sequence 5'-CACTGAACCAGAAGAAGCCATACAAACTCGCACAGTGATAAATCAGCACGG TGTATCCGAGACTCTAGTGGAGAATTTTCTCAGTAGAGCAGCTTTGG-3' (SEQ ID NO:6).

7. The method of claim 5, wherein the detectable label is a fluorescence emitting label and a fluorescence quenching label.

8. A method for detection of enterovirus D68 in a sample, the method comprising:

a) contacting a nucleic acid obtained from the sample with an oligonucleotide primer consisting essentially of the sequence 5'-CACYGAACCAGARGAAGCCA-3' (SEQ ID NO:3) and an oligonucleotide primer consisting essentially of the sequence 5'-CCAAAGCTGCTCTACTGAGAAA-3' (SEQ ID NO:10);

b) exposing the contacted sample to a DNA amplification process that provides for production of a nucleotide amplification product of 98 nucleotides in length of the enterovirus D68 VP1 gene; and c) detecting the amplification product, wherein the presence of said amplification product indicates that the sample contained enterovirus D68.

9. The method of claim 8, wherein the nucleic acid is a cDNA obtained from the sample by subjecting RNA obtained from the sample to an RT-PCR process.

10. The method of claim 8, wherein the amplification product is detected with a probe that hybridizes to the amplification product.

11. The method of claim 10, wherein the probe comprises the sequence 5'-TCGCACAGTGATAAATCAGCACGG-3' (SEQ ID NO:5) and at least one detectable label.

12. The method of claim 8, wherein the amplification product consists of the sequence 5'-CACTGAACCAGAAGAAGCCATACAAACTCGCACAGTGATAAATCAGCACGG TGTATCCGAGACTCTAGTGGAGAATTTTCTCAGTAGAGCAGCTTTGG-3' (SEQ ID NO:6).

13. The method of claim 11, wherein the detectable label is a fluorescence emitting label and a fluorescence quenching label.

* * * * *

SEQUENCE LISTING

<160> NUMBER OF SEQ ID NOS: 19

<210> SEQ ID NO 1
<211> LENGTH: 7296
<212> TYPE: DNA
<213> ORGANISM: Enterovirus 68

<400> SEQUENCE: 1
ccactccaag ggcccacgtg gcggctagta ctctggtact tcggtacctt tgtacgcctg 60
ttttatctcc cttcccaatg taacttagaa gttcttaaat caatgctcaa taggtggggc 120
gcaaaccagc gctctcatga gcaagcactc ctgtctcccc ggtgaggttg tataaactgt 180
tcccacggtt gaaaacaacc tatccgttat ccgctatagt acttcgagaa acctagtacc 240
acctttggat tgttgacgcg ttgcgctcag cacactaacc cgtgtgtagc ttgggtcgat 300
gagtctggac atacctcact ggcgacagtg gtccaggctg cgttggcggc ctactcatgg 360
tgaaagccat gagacgctag acatgaacaa ggtgtgaaga gtctattgag ctactataga 420
gtcctccggc ccctgaatgc ggctaatcct aaccatggag caagtgctca caggccagtg 480
agttgcttgt cgtaatgcgc aagtccgtgg cggaaccgac tactttgggt gtccgtgttt 540
cactttttac ttttatgact gcttatggtg acaatttgat attgttacca tttagcttgt 600
caaatcaatt gcaaaagatc ctaaatctta tttatcaact tgcatcttga taactttaat 660
ttgaaaattt taacaatggg agctcaggtt actagacaac aaactggcac tcatgaaaat 720
gccaacattg ccacaaatgg atctcatatc acatacaatc agataaactt ttacaaggat 780
agctatgcgg cttcagccag caagcaggat ttttcacagg acccatcaaa attcactgaa 840
ccagtagtgg aaggtttaaa agcaggggcg ccagttttga aatctcctag tgctgaggca 900
tgtggctaca gtgatagagt attacagctc aaattaggaa attcagctat tgtcacccag 960
gaagcagcga actactgctg cgcttatggt gaatggccca attacttacc agaccatgaa 1020
gcagtagcca ttgataaacc tacacaacca gaaactgcta cagatagatt ctacactttg 1080
aaatcagtca aatgggaaac tggaagcaca ggatggtggt ggaaactacc cgatgcactg 1140
aataatatag gcatgtttgg acagaatgtg cagcatcact acctatatag atctggtttc 1200
ttgattcatg tgcagtgtaa tgccacaaaa ttccatcaag gtgccttatt agtggtagca 1260
attccagaac atcagagggg agcgcacaac accaacacta gcccagggtt tgatgatata 1320
atgaaaggtg aagaaggagg gaccttcaat catccatatg tccttgatga tggaacatca 1380
ttggcttgtg cgacgatatt tccacatcag tggataaatc tgagaaccaa caattcagca 1440
acaattgttc ttccctggat gaatgctgct ccaatggatt tcccacttag acataatcag 1500
tggacgctag caataatacc agtggtgcca ttaggtacgc gtacaacatc aagtatggtc 1560
ccaataacag tttcaatcgc tccaatgtgt tgtgagttta atggacttag acacgccatt 1620
actcaaggtg tcccaacata ccttttacca ggctcgggac aattcctaac aactgatgat 1680
catagctctg caccagctct cccgtgtttc aacccaactc cagaaatgca tatcccaggg 1740
caggtccgta acatgctaga agtggtccaa gtggaatcaa tgatggagat taataacaca 1800
gaaagtgcag ttggcatgga gcgtcttaag gttgatatat cagcattgac agatgtcgat 1860
caattgttat tcaacattcc actggacata cagttggatg ggccacttag aaacactttg 1920
gtaggaaaca tatctagata ttacactcat tggtctggat ccctagaaat gacgtttatg 1980
ttttgtggca gcttcatggc aacgggaaaa ttaatcctgt gctatactcc tccaggtgga 2040
tcatgcccga caaccagaga gaccgccatg ttaggtacac atattgtttg ggattttgga 2100

-continued

```
ttacaatcta gtgtaaccct gataatacct tggattagtg gatcccacta caggatgttt   2160

aataatgatg ctaagtcaac taatgccaac gttggctatg tcacttgttt tatgcagacc   2220

aatctgatag tccccagtga atcctctgac acgtgttcct tgatagggtt catagcagca   2280

aaagatgatt tctccctcag attaatgaga gacagccctg acattggaca actagaccat   2340

ttacatgcag cagaggcagc ctaccagatc gagagcatca tcaaaacagc gaccgacact   2400

gtgaaaagtg agattaatgc tgaacttggt gtggtcccta gcttaaatgc agttgaaaca   2460

ggtgcaactt ctaacactga accagaagaa gccatacaaa ctcgcacagt gataaatcag   2520

cacggtgtat ccgagactct agtggagaat tttctcagta gagcagcttt ggtatcaaag   2580

agaagttttg aatacaaaga tcatacttcg tctgcagcac aagcagacaa gaactttttc   2640

aaatggacaa ttaacaccag atcctttgta cagttaagaa gaaaattaga attattcaca   2700

taccttagat ttgatgctga gatcactata ctcacaactg tagcagtgaa tggtagtggt   2760

aataatacat acgtgggtct tcctgacttg acactccaag caatgtttgt acccactggt   2820

gctcttaccc cagaaaaaca ggactcattc cactggcagt caggcagtaa tgctagtgta   2880

ttctttaaaa tctccgaccc cccagccaga ataaccatac cttttatgtg cattaactca   2940

gcatactcag tttttatga tggctttgcc ggatttgaga aaaacggtct gtatggaata   3000

aatccagctg acactattgg taacttatgt gttagaatag tgaatgaaca ccaaccagtt   3060

ggtttcacag tgaccgttag ggtttacatg aagcctaaac acataaaagc atgggcacca   3120

cgaccaccac gaactttgcc atatatgagt attgcaaatg caaattacaa aggtaaagaa   3180

agagcaccaa atgcgctcaa tgctataatt ggcaatagag acagtgtcaa aaccatgcct   3240

cataatatag tgaacactgg tccaggcttc ggaggagttt ttgtagggtc tttcaaaata   3300

atcaactatc acttggccac tacagaagag agacagtcag ctatctatgt ggattggcaa   3360

tcagacgtct tggttacccc cattgctgct catggaaggc accaaatagc aagatgcaag   3420

tgcaacacag ggggtttacta ttgtaggcac aaaaacagaa gttacccgat ttgctttgaa   3480

ggcccaggga ttcaatggat tgaacaaaat gaatattacc cagcaaggta ccagaccaat   3540

gtactattgg cagttggtcc tgcggaagca ggagattgcg gtggtttact agtttgtcca   3600

catggggtaa tcggtcttct tacagcagga gggggtggaa ttgtagcttt cactgatatc   3660

aggaatttgc tatggttaga tactgatgct atggaacaag gcattactga ttatattcaa   3720

aatcttggta atgcctttgg agcaggattt acagaaacaa tctctaataa agccaaggaa   3780

gtgcaagata tgctaattgg agagagttca ctattagaaa aattgttaaa agctctaatc   3840

aaaatcatat cagcattagt aattgtaatc agaaactcag aagatttagt cacagtcaca   3900

gccacactag cattgttggg atgccatgat tcaccatgga gctacttgaa acagaaggta   3960

tgttcatact taggtattcc ttatgtacct agacagggtg aatcgtggct taagaaattc   4020

acagaggcat gcaatgctct tagaggtctg gattggctat cgcaaaagat agataaattc   4080

atcaactggc ttaaaaccaa aatattacca gaagctaggg agaaatatga atttgtgcaa   4140

aggctcaaac agttaccggt gatagaaaac caagttagta caatcgagca tagctgccca   4200

acaacagaac aacaacaggc cttattcaac aacgtccaat actattcaca ctactgtaga   4260

aagtacgcac cactttacgc agtggaagca aagagggtag tagctcttga aaagaaaata   4320

aacaactaca tccagttcaa gtccaaatct cgcattgaac cggtttgttt aataatacat   4380

ggctctccag gaactggcaa gtcagtggct tcaaatttaa ttgccagggc tatcacagag   4440
```

aaattggggg gggacattta ttccttgcct ccagacccta aatattttga tggatacaaa 4500
cagcaaacag tggtcctcat ggatgattta atgcaaaatc cagatgggaa tgacatatct 4560
atgttctgcc aaatggtctc cactgtagat ttcatacccc caatggctag tttggaggaa 4620
aaaggaactc tatacaccag tccattttta atagctacta ccaatgctgg ctcaatacat 4680
gcaccaactg tatcagactc aaaggctttg tcacgcagat ttaaatttga cgtggacatt 4740
gaagtcacag attcatacaa ggactcaaat aaattggata tgtcaagggc agtcgagatg 4800
tgcaaaccag atggctgtgc ccccaccaat tacaaaagat gctgcccatt gatctgtgga 4860
aaggctatcc aattcagaga tcgcagaact aatgcaagat ccactattga tatgctagta 4920
actgatatta taaaggaata tagaaccaga aacagtacac aggataagct ggaagctctg 4980
tttcaggggc ctccacagtt taaagagatc aaaatttcag tcaccccaga tacaccagct 5040
cctgatgcta taaatgacct tcttaggtca gtggattctc aagaagttag ggattattgc 5100
caaaagaaag gatggattgt agtacaccca tcaaatgagc taatagtaga aaaacacatt 5160
agtagagctt ttattactct acaagccatt gccacctttg tatcaatagc tggtgtagtt 5220
tatgttatat acaaactttt tgctggcatt cagggtccat acacaggaat ccccaatcct 5280
aaacctaaag taccctctct cagaacagct aaagtgcaag gaccagggtt cgattttgca 5340
caagccataa tgaagaaaaa taccgtcatt gcaaggactg aaaagggtga gttcaccatg 5400
ctgggtgtat atgatagggt agcggtcatc cccacacacg catctgttgg agaaaccatt 5460
tacattaatg atgtagagac taaagtttta gatgcgtgtg cacttagaga cttgactgat 5520
acaaacttag agataaccat agtcaaatta gaccgtaatc aaaaatttag agatatcaga 5580
cattttctgc ccagatatga ggatgattac aatgacgctg tgcttagcgt acatacatca 5640
aaattcccaa atatgtatat cccagttgga caagtcacca attatggctt cttgaaccta 5700
ggtggtacac cgacgcaccg cattttaatg tataacttcc caacaagagc tggccagtgt 5760
ggtggtgtgg tgacaactac aggtaaggtg ataggaatac atgtaggtgg aaatggagct 5820
caaggatttg cagcaatgct actacactct tacttttccg atacacaagg tgagatagtt 5880
agtagtgaaa agagtggggt gtgcattaac gcaccggcaa agactaaact ccaacctagt 5940
gttttccatc aagtttttga aggttcaaag gaaccagcag ttctcaatcc aaaagatcct 6000
aggcttaaaa cagatttcga ggaggccatt ttctcaaagt acacaggtaa caaaattatg 6060
ttaatggatg agtacatgga agaggcagtg gatcattatg tggggtgttt agaaccatta 6120
gacatcagtg tggatcccat acccctggaa agtgccatgt atggaatgga tggccttgag 6180
gcattagact taactaccag tgcaggattc ccttacttac tacaagggaa gaagaaaagg 6240
gatatattta atagacatac tagagacacc agtgaaatga caaaaatgtt agagaaatat 6300
ggagttgacc taccttttgt aacctttgta aaagatgagc ttagatcaag agaaaaagtt 6360
gaaaaaggga aatcacgcct gattgaggcc agttccttga atgactcagt tgctatgaga 6420
gttgcctttg gaaaccttta cgccacattt cacaacaatc caggtacagc aactggtagt 6480
gcagttggtt gtgatccaga tatattttgg tcaaaaatcc ctattttgtt agatggagaa 6540
atctttgctt ttgactacac tggttatgat gctagtttgt caccagtgtg gtttgcctgc 6600
ttaaagaaag ttctaattaa gttaggttac acacatcaaa cgtcttttat agattatttg 6660
tgtcattcag tacatttata taaggacaaa aaatacatag ttaatggtgg aatgccctct 6720
ggttcttcag gcaccagcat attcaacact atgatcaaca atataatcat aagaacttta 6780
ttaattaggg tttacaaagg catagacctg gaccagttca aaatgattgc ctatggggat 6840

-continued

```
gatgttattg ctagctaccc acataagatt gatccaggtt tgctggcaga agcaggtaaa   6900

cagtatggat tagtaatgac gccagcagac aaaggaacca gttttattga cacaaattgg   6960

gaaaatgtaa ctttcttaaa aagatatttc agagcagatg atcaataccc ctttctcata   7020

catccagtga tgccaatgaa agagatacat gaatctatta gatggactaa agatcccaga   7080

aacacacagg atcatgttag gtctttgtgc tacctcgcat ggcataatgg agaggaggct   7140

tataatgaat tttgcagaaa aatcagaagt gtgcctgtgg gaagagcatt gacactacct   7200

gcatactcta gtcttagacg gaaatggtta gattcgttct agacaactct aattgaaacc   7260

caagttatag ttactttcat ttagaggtaa attttg                              7296
```

```
<210> SEQ ID NO 2
<211> LENGTH: 2188
<212> TYPE: PRT
<213> ORGANISM: Enterovirus 68

<400> SEQUENCE: 2

Met Gly Ala Gln Val Thr Arg Gln Gln Thr Gly Thr His Glu Asn Ala
1               5                   10                  15

Asn Ile Ala Thr Asn Gly Ser His Ile Thr Tyr Asn Gln Ile Asn Phe
            20                  25                  30

Tyr Lys Asp Ser Tyr Ala Ala Ser Ala Ser Lys Gln Asp Phe Ser Gln
        35                  40                  45

Asp Pro Ser Lys Phe Thr Glu Pro Val Val Glu Gly Leu Lys Ala Gly
    50                  55                  60

Ala Pro Val Leu Lys Ser Pro Ser Ala Glu Ala Cys Gly Tyr Ser Asp
65                  70                  75                  80

Arg Val Leu Gln Leu Lys Leu Gly Asn Ser Ala Ile Val Thr Gln Glu
                85                  90                  95

Ala Ala Asn Tyr Cys Cys Ala Tyr Gly Glu Trp Pro Asn Tyr Leu Pro
            100                 105                 110

Asp His Glu Ala Val Ala Ile Asp Lys Pro Thr Gln Pro Glu Thr Ala
        115                 120                 125

Thr Asp Arg Phe Tyr Thr Leu Lys Ser Val Lys Trp Glu Thr Gly Ser
    130                 135                 140

Thr Gly Trp Trp Trp Lys Leu Pro Asp Ala Leu Asn Asn Ile Gly Met
145                 150                 155                 160

Phe Gly Gln Asn Val Gln His His Tyr Leu Tyr Arg Ser Gly Phe Leu
                165                 170                 175

Ile His Val Gln Cys Asn Ala Thr Lys Phe His Gln Gly Ala Leu Leu
            180                 185                 190

Val Val Ala Ile Pro Glu His Gln Arg Gly Ala His Asn Thr Asn Thr
        195                 200                 205

Ser Pro Gly Phe Asp Asp Ile Met Lys Gly Glu Glu Gly Gly Thr Phe
    210                 215                 220

Asn His Pro Tyr Val Leu Asp Asp Gly Thr Ser Leu Ala Cys Ala Thr
225                 230                 235                 240

Ile Phe Pro His Gln Trp Ile Asn Leu Arg Thr Asn Asn Ser Ala Thr
                245                 250                 255

Ile Val Leu Pro Trp Met Asn Ala Ala Pro Met Asp Phe Pro Leu Arg
            260                 265                 270

His Asn Gln Trp Thr Leu Ala Ile Ile Pro Val Val Pro Leu Gly Thr
        275                 280                 285
```

-continued

```
Arg Thr Thr Ser Ser Met Val Pro Ile Thr Val Ser Ile Ala Pro Met
    290                 295                 300

Cys Cys Glu Phe Asn Gly Leu Arg His Ala Ile Thr Gln Gly Val Pro
305                 310                 315                 320

Thr Tyr Leu Leu Pro Gly Ser Gly Gln Phe Leu Thr Thr Asp Asp His
                325                 330                 335

Ser Ser Ala Pro Ala Leu Pro Cys Phe Asn Pro Thr Pro Glu Met His
            340                 345                 350

Ile Pro Gly Gln Val Arg Asn Met Leu Glu Val Val Gln Val Glu Ser
        355                 360                 365

Met Met Glu Ile Asn Asn Thr Glu Ser Ala Val Gly Met Glu Arg Leu
    370                 375                 380

Lys Val Asp Ile Ser Ala Leu Thr Asp Val Asp Gln Leu Leu Phe Asn
385                 390                 395                 400

Ile Pro Leu Asp Ile Gln Leu Asp Gly Pro Leu Arg Asn Thr Leu Val
                405                 410                 415

Gly Asn Ile Ser Arg Tyr Tyr Thr His Trp Ser Gly Ser Leu Glu Met
            420                 425                 430

Thr Phe Met Phe Cys Gly Ser Phe Met Ala Thr Gly Lys Leu Ile Leu
        435                 440                 445

Cys Tyr Thr Pro Pro Gly Gly Ser Cys Pro Thr Thr Arg Glu Thr Ala
    450                 455                 460

Met Leu Gly Thr His Ile Val Trp Asp Phe Gly Leu Gln Ser Ser Val
465                 470                 475                 480

Thr Leu Ile Ile Pro Trp Ile Ser Gly Ser His Tyr Arg Met Phe Asn
                485                 490                 495

Asn Asp Ala Lys Ser Thr Asn Ala Asn Val Gly Tyr Val Thr Cys Phe
            500                 505                 510

Met Gln Thr Asn Leu Ile Val Pro Ser Glu Ser Ser Asp Thr Cys Ser
        515                 520                 525

Leu Ile Gly Phe Ile Ala Ala Lys Asp Asp Phe Ser Leu Arg Leu Met
    530                 535                 540

Arg Asp Ser Pro Asp Ile Gly Gln Leu Asp His Leu His Ala Ala Glu
545                 550                 555                 560

Ala Ala Tyr Gln Ile Glu Ser Ile Ile Lys Thr Ala Thr Asp Thr Val
                565                 570                 575

Lys Ser Glu Ile Asn Ala Glu Leu Gly Val Val Pro Ser Leu Asn Ala
            580                 585                 590

Val Glu Thr Gly Ala Thr Ser Asn Thr Glu Pro Glu Glu Ala Ile Gln
        595                 600                 605

Thr Arg Thr Val Ile Asn Gln His Gly Val Ser Glu Thr Leu Val Glu
    610                 615                 620

Asn Phe Leu Ser Arg Ala Ala Leu Val Ser Lys Arg Ser Phe Glu Tyr
625                 630                 635                 640

Lys Asp His Thr Ser Ser Ala Ala Gln Ala Asp Lys Asn Phe Phe Lys
                645                 650                 655

Trp Thr Ile Asn Thr Arg Ser Phe Val Gln Leu Arg Arg Lys Leu Glu
            660                 665                 670

Leu Phe Thr Tyr Leu Arg Phe Asp Ala Glu Ile Thr Ile Leu Thr Thr
        675                 680                 685

Val Ala Val Asn Gly Ser Gly Asn Asn Thr Tyr Val Gly Leu Pro Asp
    690                 695                 700

Leu Thr Leu Gln Ala Met Phe Val Pro Thr Gly Ala Leu Thr Pro Glu
```

-continued

```
705                 710                 715                 720

Lys Gln Asp Ser Phe His Trp Gln Ser Gly Ser Asn Ala Ser Val Phe
                725                 730                 735

Phe Lys Ile Ser Asp Pro Pro Ala Arg Ile Thr Ile Pro Phe Met Cys
            740                 745                 750

Ile Asn Ser Ala Tyr Ser Val Phe Tyr Asp Gly Phe Ala Gly Phe Glu
        755                 760                 765

Lys Asn Gly Leu Tyr Gly Ile Asn Pro Ala Asp Thr Ile Gly Asn Leu
    770                 775                 780

Cys Val Arg Ile Val Asn Glu His Gln Pro Val Gly Phe Thr Val Thr
785                 790                 795                 800

Val Arg Val Tyr Met Lys Pro Lys His Ile Lys Ala Trp Ala Pro Arg
                805                 810                 815

Pro Pro Arg Thr Leu Pro Tyr Met Ser Ile Ala Asn Ala Asn Tyr Lys
            820                 825                 830

Gly Lys Glu Arg Ala Pro Asn Ala Leu Asn Ala Ile Ile Gly Asn Arg
        835                 840                 845

Asp Ser Val Lys Thr Met Pro His Asn Ile Val Asn Thr Gly Pro Gly
    850                 855                 860

Phe Gly Gly Val Phe Val Gly Ser Phe Lys Ile Ile Asn Tyr His Leu
865                 870                 875                 880

Ala Thr Thr Glu Glu Arg Gln Ser Ala Ile Tyr Val Asp Trp Gln Ser
                885                 890                 895

Asp Val Leu Val Thr Pro Ile Ala Ala His Gly Arg His Gln Ile Ala
            900                 905                 910

Arg Cys Lys Cys Asn Thr Gly Val Tyr Tyr Cys Arg His Lys Asn Arg
        915                 920                 925

Ser Tyr Pro Ile Cys Phe Glu Gly Pro Gly Ile Gln Trp Ile Glu Gln
    930                 935                 940

Asn Glu Tyr Tyr Pro Ala Arg Tyr Gln Thr Asn Val Leu Leu Ala Val
945                 950                 955                 960

Gly Pro Ala Glu Ala Gly Asp Cys Gly Gly Leu Leu Val Cys Pro His
                965                 970                 975

Gly Val Ile Gly Leu Leu Thr Ala Gly Gly Gly Gly Ile Val Ala Phe
            980                 985                 990

Thr Asp Ile Arg Asn Leu Leu Trp  Leu Asp Thr Asp Ala  Met Glu Gln
        995                 1000                1005

Gly Ile  Thr Asp Tyr Ile Gln  Asn Leu Gly Asn Ala  Phe Gly Ala
    1010                1015                1020

Gly Phe  Thr Glu Thr Ile Ser  Asn Lys Ala Lys Glu  Val Gln Asp
    1025                1030                1035

Met Leu  Ile Gly Glu Ser Ser  Leu Leu Glu Lys Leu  Leu Lys Ala
    1040                1045                1050

Leu Ile  Lys Ile Ile Ser Ala  Leu Val Ile Val Ile  Arg Asn Ser
    1055                1060                1065

Glu Asp  Leu Val Thr Val Thr  Ala Thr Leu Ala Leu  Leu Gly Cys
    1070                1075                1080

His Asp  Ser Pro Trp Ser Tyr  Leu Lys Gln Lys Val  Cys Ser Tyr
    1085                1090                1095

Leu Gly  Ile Pro Tyr Val Pro  Arg Gln Gly Glu Ser  Trp Leu Lys
    1100                1105                1110

Lys Phe  Thr Glu Ala Cys Asn  Ala Leu Arg Gly Leu  Asp Trp Leu
    1115                1120                1125
```

-continued

```
Ser Gln  Lys Ile Asp Lys Phe  Ile Asn Trp Leu Lys  Thr Lys Ile
    1130                 1135                 1140

Leu Pro  Glu Ala Arg Glu Lys  Tyr Glu Phe Val Gln  Arg Leu Lys
    1145                 1150                 1155

Gln Leu  Pro Val Ile Glu Asn  Gln Val Ser Thr Ile  Glu His Ser
    1160                 1165                 1170

Cys Pro  Thr Thr Glu Gln Gln  Gln Ala Leu Phe Asn  Asn Val Gln
    1175                 1180                 1185

Tyr Tyr  Ser His Tyr Cys Arg  Lys Tyr Ala Pro Leu  Tyr Ala Val
    1190                 1195                 1200

Glu Ala  Lys Arg Val Val Ala  Leu Glu Lys Lys Ile  Asn Asn Tyr
    1205                 1210                 1215

Ile Gln  Phe Lys Ser Lys Ser  Arg Ile Glu Pro Val  Cys Leu Ile
    1220                 1225                 1230

Ile His  Gly Ser Pro Gly Thr  Gly Lys Ser Val Ala  Ser Asn Leu
    1235                 1240                 1245

Ile Ala  Arg Ala Ile Thr Glu  Lys Leu Gly Gly Asp  Ile Tyr Ser
    1250                 1255                 1260

Leu Pro  Pro Asp Pro Lys Tyr  Phe Asp Gly Tyr Lys  Gln Gln Thr
    1265                 1270                 1275

Val Val  Leu Met Asp Asp Leu  Met Gln Asn Pro Asp  Gly Asn Asp
    1280                 1285                 1290

Ile Ser  Met Phe Cys Gln Met  Val Ser Thr Val Asp  Phe Ile Pro
    1295                 1300                 1305

Pro Met  Ala Ser Leu Glu Glu  Lys Gly Thr Leu Tyr  Thr Ser Pro
    1310                 1315                 1320

Phe Leu  Ile Ala Thr Thr Asn  Ala Gly Ser Ile His  Ala Pro Thr
    1325                 1330                 1335

Val Ser  Asp Ser Lys Ala Leu  Ser Arg Arg Phe Lys  Phe Asp Val
    1340                 1345                 1350

Asp Ile  Glu Val Thr Asp Ser  Tyr Lys Asp Ser Asn  Lys Leu Asp
    1355                 1360                 1365

Met Ser  Arg Ala Val Glu Met  Cys Lys Pro Asp Gly  Cys Ala Pro
    1370                 1375                 1380

Thr Asn  Tyr Lys Arg Cys Cys  Pro Leu Ile Cys Gly  Lys Ala Ile
    1385                 1390                 1395

Gln Phe  Arg Asp Arg Arg Thr  Asn Ala Arg Ser Thr  Ile Asp Met
    1400                 1405                 1410

Leu Val  Thr Asp Ile Ile Lys  Glu Tyr Arg Thr Arg  Asn Ser Thr
    1415                 1420                 1425

Gln Asp  Lys Leu Glu Ala Leu  Phe Gln Gly Pro Pro  Gln Phe Lys
    1430                 1435                 1440

Glu Ile  Lys Ile Ser Val Thr  Pro Asp Thr Pro Ala  Pro Asp Ala
    1445                 1450                 1455

Ile Asn  Asp Leu Leu Arg Ser  Val Asp Ser Gln Glu  Val Arg Asp
    1460                 1465                 1470

Tyr Cys  Gln Lys Lys Gly Trp  Ile Val Val His Pro  Ser Asn Glu
    1475                 1480                 1485

Leu Ile  Val Glu Lys His Ile  Ser Arg Ala Phe Ile  Thr Leu Gln
    1490                 1495                 1500

Ala Ile  Ala Thr Phe Val Ser  Ile Ala Gly Val Val  Tyr Val Ile
    1505                 1510                 1515
```

-continued

```
Tyr Lys  Leu Phe Ala Gly Ile  Gln Gly Pro Tyr Thr  Gly Ile Pro
    1520                 1525                 1530

Asn Pro  Lys Pro Lys Val Pro  Ser Leu Arg Thr Ala  Lys Val Gln
    1535                 1540                 1545

Gly Pro  Gly Phe Asp Phe Ala  Gln Ala Ile Met Lys  Lys Asn Thr
    1550                 1555                 1560

Val Ile  Ala Arg Thr Glu Lys  Gly Glu Phe Thr Met  Leu Gly Val
    1565                 1570                 1575

Tyr Asp  Arg Val Ala Val Ile  Pro Thr His Ala Ser  Val Gly Glu
    1580                 1585                 1590

Thr Ile  Tyr Ile Asn Asp Val  Glu Thr Lys Val Leu  Asp Ala Cys
    1595                 1600                 1605

Ala Leu  Arg Asp Leu Thr Asp  Thr Asn Leu Glu Ile  Thr Ile Val
    1610                 1615                 1620

Lys Leu  Asp Arg Asn Gln Lys  Phe Arg Asp Ile Arg  His Phe Leu
    1625                 1630                 1635

Pro Arg  Tyr Glu Asp Asp Tyr  Asn Asp Ala Val Leu  Ser Val His
    1640                 1645                 1650

Thr Ser  Lys Phe Pro Asn Met  Tyr Ile Pro Val Gly  Gln Val Thr
    1655                 1660                 1665

Asn Tyr  Gly Phe Leu Asn Leu  Gly Gly Thr Pro Thr  His Arg Ile
    1670                 1675                 1680

Leu Met  Tyr Asn Phe Pro Thr  Arg Ala Gly Gln Cys  Gly Gly Val
    1685                 1690                 1695

Val Thr  Thr Thr Gly Lys Val  Ile Gly Ile His Val  Gly Gly Asn
    1700                 1705                 1710

Gly Ala  Gln Gly Phe Ala Ala  Met Leu Leu His Ser  Tyr Phe Ser
    1715                 1720                 1725

Asp Thr  Gln Gly Glu Ile Val  Ser Ser Glu Lys Ser  Gly Val Cys
    1730                 1735                 1740

Ile Asn  Ala Pro Ala Lys Thr  Lys Leu Gln Pro Ser  Val Phe His
    1745                 1750                 1755

Gln Val  Phe Glu Gly Ser Lys  Glu Pro Ala Val Leu  Asn Pro Lys
    1760                 1765                 1770

Asp Pro  Arg Leu Lys Thr Asp  Phe Glu Glu Ala Ile  Phe Ser Lys
    1775                 1780                 1785

Tyr Thr  Gly Asn Lys Ile Met  Leu Met Asp Glu Tyr  Met Glu Glu
    1790                 1795                 1800

Ala Val  Asp His Tyr Val Gly  Cys Leu Glu Pro Leu  Asp Ile Ser
    1805                 1810                 1815

Val Asp  Pro Ile Pro Leu Glu  Ser Ala Met Tyr Gly  Met Asp Gly
    1820                 1825                 1830

Leu Glu  Ala Leu Asp Leu Thr  Thr Ser Ala Gly Phe  Pro Tyr Leu
    1835                 1840                 1845

Leu Gln  Gly Lys Lys Lys Arg  Asp Ile Phe Asn Arg  His Thr Arg
    1850                 1855                 1860

Asp Thr  Ser Glu Met Thr Lys  Met Leu Glu Lys Tyr  Gly Val Asp
    1865                 1870                 1875

Leu Pro  Phe Val Thr Phe Val  Lys Asp Glu Leu Arg  Ser Arg Glu
    1880                 1885                 1890

Lys Val  Glu Lys Gly Lys Ser  Arg Leu Ile Glu Ala  Ser Ser Leu
    1895                 1900                 1905

Asn Asp  Ser Val Ala Met Arg  Val Ala Phe Gly Asn  Leu Tyr Ala
```

1910 1915 1920

Thr Phe His Asn Asn Pro Gly Thr Ala Thr Gly Ser Ala Val Gly
1925 1930 1935

Cys Asp Pro Asp Ile Phe Trp Ser Lys Ile Pro Ile Leu Leu Asp
1940 1945 1950

Gly Glu Ile Phe Ala Phe Asp Tyr Thr Gly Tyr Asp Ala Ser Leu
1955 1960 1965

Ser Pro Val Trp Phe Ala Cys Leu Lys Lys Val Leu Ile Lys Leu
1970 1975 1980

Gly Tyr Thr His Gln Thr Ser Phe Ile Asp Tyr Leu Cys His Ser
1985 1990 1995

Val His Leu Tyr Lys Asp Lys Lys Tyr Ile Val Asn Gly Gly Met
2000 2005 2010

Pro Ser Gly Ser Ser Gly Thr Ser Ile Phe Asn Thr Met Ile Asn
2015 2020 2025

Asn Ile Ile Ile Arg Thr Leu Leu Ile Arg Val Tyr Lys Gly Ile
2030 2035 2040

Asp Leu Asp Gln Phe Lys Met Ile Ala Tyr Gly Asp Asp Val Ile
2045 2050 2055

Ala Ser Tyr Pro His Lys Ile Asp Pro Gly Leu Leu Ala Glu Ala
2060 2065 2070

Gly Lys Gln Tyr Gly Leu Val Met Thr Pro Ala Asp Lys Gly Thr
2075 2080 2085

Ser Phe Ile Asp Thr Asn Trp Glu Asn Val Thr Phe Leu Lys Arg
2090 2095 2100

Tyr Phe Arg Ala Asp Asp Gln Tyr Pro Phe Leu Ile His Pro Val
2105 2110 2115

Met Pro Met Lys Glu Ile His Glu Ser Ile Arg Trp Thr Lys Asp
2120 2125 2130

Pro Arg Asn Thr Gln Asp His Val Arg Ser Leu Cys Tyr Leu Ala
2135 2140 2145

Trp His Asn Gly Glu Glu Ala Tyr Asn Glu Phe Cys Arg Lys Ile
2150 2155 2160

Arg Ser Val Pro Val Gly Arg Ala Leu Thr Leu Pro Ala Tyr Ser
2165 2170 2175

Ser Leu Arg Arg Lys Trp Leu Asp Ser Phe
2180 2185

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (4)..(4)
<223> OTHER INFORMATION: Y=T,C
<220> FEATURE:
<221> NAME/KEY: misc_feature
<222> LOCATION: (13)..(13)
<223> OTHER INFORMATION: R=G,A

<400> SEQUENCE: 3
cacygaacca gargaagcca 20

<210> SEQ ID NO 4
<211> LENGTH: 22

```
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (3)..(3)
<223> OTHER INFORMATION: R=G,A

<400> SEQUENCE: 4

aargaatcat cccgtcgaaa tc                                              22


<210> SEQ ID NO 5
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 5

tcgcacagtg ataaatcagc acgg                                            24


<210> SEQ ID NO 6
<211> LENGTH: 98
<212> TYPE: DNA
<213> ORGANISM: Artificial Sequence
<220> FEATURE:
<223> OTHER INFORMATION: SYNTHESIZED

<400> SEQUENCE: 6

cactgaacca gaagaagcca tacaaactcg cacagtgata aatcagcacg gtgtatccga     60

gactctagtg gagaattttc tcagtagagc agctttgg                             98


<210> SEQ ID NO 7
<211> LENGTH: 23
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (3)..(3)
<223> OTHER INFORMATION: R=G,A

<400> SEQUENCE: 7

ggrttcatag cagcaaaaga tga                                             23


<210> SEQ ID NO 8
<211> LENGTH: 25
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (5)..(5)
<223> OTHER INFORMATION: Y=T,C
<220> FEATURE:
<221> NAME/KEY: misc_feature
<222> LOCATION: (20)..(20)
<223> OTHER INFORMATION: R=G,A

<400> SEQUENCE: 8

taggyttcat gtaaaccctr acrgt                                           25


<210> SEQ ID NO 9
<211> LENGTH: 20
<212> TYPE: DNA
```

-continued

<213> ORGANISM: Artificial Sequence
<220> FEATURE:
<223> OTHER INFORMATION: SYNTHESIZED

<400> SEQUENCE: 9
cactgaacca gaagaagcca 20

<210> SEQ ID NO 10
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 10
ccaaagctgc tctactgaga aa 22

<210> SEQ ID NO 11
<211> LENGTH: 22
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (20)..(20)
<223> OTHER INFORMATION: R=G,A

<400> SEQUENCE: 11
ctaaagctgc cctactaagr aa 22

<210> SEQ ID NO 12
<211> LENGTH: 24
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (22)..(22)
<223> OTHER INFORMATION: Y=T,C

<400> SEQUENCE: 12
tcgcacagtg ataaatcagc aygg 24

<210> SEQ ID NO 13
<211> LENGTH: 109
<212> TYPE: DNA
<213> ORGANISM: Enterovirus 68

<400> SEQUENCE: 13
caacttctaa cactgaacca gaagaagcca tacaaactcg cacagtgata aatcagcacg 60
gtgtatccga gactctagtg gagaattttc tcagtagagc agctttggt 109

<210> SEQ ID NO 14
<211> LENGTH: 109
<212> TYPE: DNA
<213> ORGANISM: Enterovirus 68

<400> SEQUENCE: 14
accaaagctg ctctactgag aaaattctcc actagagtct cggatacacc gtgctgattt 60
atcactgtgc gagtttgtat ggcttcttct ggttcagtgt tagaagttg 109

<210> SEQ ID NO 15
<211> LENGTH: 26

<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (21)..(21)
<223> OTHER INFORMATION: Y=T,C
<220> FEATURE:
<221> NAME/KEY: misc_feature
<222> LOCATION: (24)..(24)
<223> OTHER INFORMATION: R=G,A

<400> SEQUENCE: 15
caaactcgca cagtgataaa ycarca 26

<210> SEQ ID NO 16
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 16
ctgttcttga aaaagtttac ctg 23

<210> SEQ ID NO 17
<211> LENGTH: 29
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 17
gtattattac tactaccatt cacngcnac 29

<210> SEQ ID NO 18
<211> LENGTH: 313
<212> TYPE: DNA
<213> ORGANISM: Enterovirus 68

<400> SEQUENCE: 18
aacttctaac actgaaccag aagaagccat acaaactcgc acagtgataa atcagcacgg 60
tgtatccgag actctagtgg agaattttct cagtagagca gctttggtat caaagagaag 120
ttttgaatac aaagatcata cttcgtctgc agcacaagca gacaagaact ttttcaaatg 180
gacaattaac accagatcct ttgtacagtt aagaagaaaa ttagaattat tcacatacct 240
tagatttgat gctgagatca ctatactcac aactgtagca gtgaatggta gtggtaataa 300
tacatacgtg ggt 313

<210> SEQ ID NO 19
<211> LENGTH: 314
<212> TYPE: DNA
<213> ORGANISM: Enterovirus 68

<400> SEQUENCE: 19
acccacgtat gtattattac cactaccatt cactgctaca gttgtgagta tagtgatctc 60

-continued

| | |
|---|---|
| agcatcaaat ctaaggtatg tgaataattc taattttctt cttaactgta caaaggatct | 120 |
| ggtgttaatt gtccatttga aaaagttctt gtctgcttgt gctgcagacg aagtatgatc | 180 |
| tttgtattca aaacttctct ttgataccaa agctgctcta ctgagaaaat tctccactag | 240 |
| agtctcggat acaccgtgct gatttatcac tgtgcgagtt tgtatggctt cttctggttc | 300 |
| agtgttagaa gttg | 314 |